United States Patent
Sakaida

(10) Patent No.: US 8,295,568 B2
(45) Date of Patent: Oct. 23, 2012

(54) MEDICAL IMAGE DISPLAY PROCESSING APPARATUS AND MEDICAL IMAGE DISPLAY PROCESSING PROGRAM

(75) Inventor: Hideyuki Sakaida, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 845 days.

(21) Appl. No.: 12/306,891

(22) PCT Filed: Jun. 26, 2007

(86) PCT No.: PCT/JP2007/063205
§ 371 (c)(1),
(2), (4) Date: May 1, 2009

(87) PCT Pub. No.: WO2008/001928
PCT Pub. Date: Jan. 3, 2008

(65) Prior Publication Data
US 2009/0279753 A1 Nov. 12, 2009

(30) Foreign Application Priority Data

Jun. 30, 2006 (JP) .................................. 2006-181608
Jun. 30, 2006 (JP) .................................. 2006-181609

(51) Int. Cl.
*G06K 9/00* (2006.01)
(52) U.S. Cl. ......... 382/128; 328/128; 328/131; 328/133
(58) Field of Classification Search .................. 382/128, 382/131, 132; 600/438
See application file for complete search history.

(56) References Cited

U.S. PATENT DOCUMENTS

| 6,904,163 B1 * | 6/2005 | Fujimura et al. .............. 382/131 |
| 2004/0081341 A1 * | 4/2004 | Cherek et al. ................. 382/128 |
| 2005/0227154 A1 * | 10/2005 | Motoki ........................... 430/22 |

FOREIGN PATENT DOCUMENTS

| JP | 08-294485 A | 11/1996 |
| JP | 11-085950 A | 3/1999 |
| JP | 2000-116604 A | 4/2000 |
| JP | 2001-076141 A | 3/2001 |
| JP | 2001-120541 A | 5/2001 |
| JP | 2002-253539 A | 9/2002 |
| JP | 2004-167042 A | 6/2004 |

* cited by examiner

*Primary Examiner* — Marcos D. Pizarro
*Assistant Examiner* — Suian Tang
(74) *Attorney, Agent, or Firm* — Sughrue Mion, PLLC

(57) ABSTRACT

An medical image display processing apparatus capable of easily displaying an axial image of a body part desired by a user from among one series of axial images acquired by imaging an object to be inspected with a modality. The medical image display processing apparatus includes a part recognition unit for recognizing a body part shown in each of one series of axial images; and a display processing unit for causing the display unit to display an axial image included in the one series of axial images, and causing, when receiving a body part change instruction, the display unit to display an axial image showing a different part from the part of the axial image being displayed on the display unit based on a recognition result of the part recognition unit.

28 Claims, 15 Drawing Sheets

| AMOUNT OF AIR | 0~10% | 10~40% | 40~80% | 80~100% |
|---|---|---|---|---|
| HEAD | 0.9 | -1.0 | -1.0 | -1.0 |
| CHEST | -1.0 | 0.0 | 0.8 | 1.0 |
| ABDOMEN | -1.0 | 0.8 | -0.2 | -1.0 |
| LEG | 1.0 | -1.0 | -1.0 | -1.0 |

UPPER SECTION

▨ : HEAD
☐ : NECK
▩ : CHEST
☰ : ABDOMEN

LOWER SECTION

SLICE
NUMBER:

| 1 | 2 | 3 | 4 | 5 | 6 | 7 | 8 | 9 | 19 | 11 | 12 | 13 | 14 | 15 | PART |
|---|---|---|---|---|---|---|---|---|----|----|----|----|----|----|------|
|0.0|0.0|0.7|0.3|0.8|0.2|0.6|0.7|0.9|1.3|1.5|2.1|1.6|1.4|1.8| HEAD |
|0.2|0.5|0.0|0.0|0.0|0.7|0.0|0.9|0.4|0.7|0.4|0.7|0.9|1.2|1.1| NECK |
|0.3|0.9|0.6|0.7|0.4|0.0|0.5|0.0|0.0|0.3|0.0|0.3|0.7|1.1|1.3| CHEST |
|1.0|1.4|1.1|1.7|1.3|0.6|0.9|0.3|0.7|0.0|0.2|0.0|0.0|0.0|0.0| ABDOMEN |

SLICE
NUMBER:

| 1 | 2 | 3 | 4 | 5 | 6 | 7 | 8 | 9 | 19 | 11 | 12 | 13 | 14 | 15 | PART |
|---|---|---|---|---|---|---|---|---|----|----|----|----|----|----|------|
|0.0|0.0|0.0|0.7|0.3|0.8|0.2|0.6|0.7|0.9|1.3|1.5|2.1|1.6|1.4| HEAD |
|0.0|0.5|0.0|0.0|0.7|1.0|0.8|1.1|1.0|1.4|1.3|2.0|2.4|3.3|2.7| NECK |
|0.2|0.9|1.1|0.7|0.4|0.7|1.5|0.8|1.1|1.3|1.4|1.6|2.7|3.5|4.6| CHEST |
|0.3|1.6|2.0|2.8|2.0|1.0|1.6|1.8|1.5|1.1|1.5|1.4|1.6|2.7|3.5| ABDOMAN |

IMAGE AT THIS INSPECTION　　　IMAGE AT PREVIOUS INSPECTION

IMAGE AT THIS INSPECTION　　　IMAGE AT PREVIOUS INSPECTION

MEDICAL IMAGE DISPLAY PROCESSING APPARATUS AND MEDICAL IMAGE DISPLAY PROCESSING PROGRAM

CROSS REFERENCE TO RELATED APPLICATIONS

This application is a National Stage of International Application No. PCT/JP2007/063205 filed Jun. 26, 2007, claiming priority based on Japanese Patent Application Nos. 2006-181608 filed Jun. 30, 2006 and 2006-181609 filed Jun. 30, 2006, the contents of all of which are incorporated herein by reference in their entirety.

TECHNICAL FIELD

The present invention relates to a medical image display processing apparatus for displaying medical images based on image data acquired by a medical imaging modality, and a medical image display processing program to be used in the apparatus.

BACKGROUND ART

Recent years, many medical images showing the interiors of living bodies have been used in medical diagnoses, and, in order to acquire such medical images, various technologies and apparatuses (modalities) such as an X-ray imaging apparatus, X-ray CT (computed tomography) apparatus, ultrasonic (US) diagnostic apparatus, MRI (magnetic resonance imaging) apparatus, and PET (positron emission tomography) apparatus are widely used. Many of the apparatuses are digitalized, and diagnostic information processing systems within hospitals and so on are being constructed. Further, among the imaging technologies, CT and MRI have achieved significant results in detection and evaluation of lesion parts in living bodies because they can acquire and display axial images of a living body at relatively short intervals. Here, an axial image refers to a tomographic image that shows a surface perpendicular or substantially perpendicular to the body axis of an object to be inspected (so-called cross sectional surface). Hereinafter, the axial image is also simply referred to as "slice image".

At the time of tomographic imaging for CT inspection or the like, not only one part (e.g., only the chest or abdomen) is necessarily imaged, but imaging is often performed over plural parts (e.g., from chest to abdomen, head to chest, or the like) in one inspection. One series of slice images obtained by imaging are typically a thousand and several hundreds to several thousands of images, and therefore, significant effort and burden are taken for display slice images of a part desired by an image interpretation doctor.

As a related technology, the applicant has proposed an image display apparatus capable of reproduction display of sectional images designated by a user (see Japanese Patent Application Publication JP-P2004-167042A). This image display apparatus is an image display apparatus for sequentially displaying plural sectional images continuous in an axis direction while moving the section of the sectional image to be displayed along a direction perpendicular to the section based on three-dimensional image data representing a subject, including designating means for designating a sectional image desired by the user among the sequentially displayed plural sectional images, first storing means for storing a first display parameter for display of the sectional image including a position in the direction perpendicular to the section of the sectional image designated by the designating means, and first image displaying means for displaying the designated sectional image based on the first display parameter stored by the first storing means according to a request of the user (page 2, FIG. 2).

That is, in JP-P2004-167042A, the user designates the desired sectional image, stores the first display parameter for display of the designated sectional image, and displays the designated sectional image based on the stored first display parameter. For the purpose, the user is necessary to designate the sectional image desired by the user. However, one series of slice images are typically a thousand and several hundreds to several thousands of images, and therefore, significant effort and burden are taken for the user to designate the desired slice image.

Further, Japanese Patent Application Publication JP-P2002-253539A discloses a system for enabling efficient management of an enormous amount of medical images by automatically extracting imaging attribute information of imaging apparatus, part, imaging orientation, and so on by image processing from medical images, and adding the information to management information. The medical image identification system is a system for storing and managing medical images, and includes means for classifying an input image, template image storing means for storing template images on categories to be identified with respect to each classification, means for selecting template images of plural categories as candidates of identification using the classification result of the input image, image identifying means for comparing the selected template images with the input image and determining the category of the template image that is the best match, and means for adding manage information the template image has to management information of the input image (page 2, FIG. 1).

That is, in JP-P2002-253539A, the imaged part or the like of the input image is determined by classifying the input image based on the size of the input image, the number of rectangular areas in the input image, and so on, selecting template images of plural categories according to the classification, extracting one that matches the gray scale information and the mosaic image of the input image from the selected template images, and providing the management information (e.g., the imaged part) that has been provided to the template image as management information of the input image.

However, one medical image does not always show only one part. For example, plural parts are often shown in the way that the chest is shown in a portion of an image and the abdomen is shown in another portion of the image. Despite this, JP-P2002-253539A does not disclose anything about part recognition for images that show plural parts.

On the other hand, for a follow-up of a disease or the like, plural times of tomographic imaging on one patient may be performed at great time intervals. In this case, an image interpretation doctor compares slice images obtained at this inspection and slice images obtained at the previous inspection (comparison interpretation), and thereby, can more properly grasp the progress of the disease or the like. Accordingly, conventionally, a medical image display apparatus on which the slice images obtained at this inspection and slice images obtained at the previous inspection are displayed side by side is used.

In such a conventional medical image display apparatus, the image interpretation doctor associates one slice image of the one series of slice images obtained at this inspection with one slice image of one series of slice images obtained at the previous inspection, and allows to display other slice images based on the pair of associated slice images. For example, the image interpretation doctor associates the slice image being displayed within the first area of the display screen (the slice image showing the abdomen part obtained at this inspection) with the slice image being displayed within the second area of the display screen (the slice image showing the abdomen part obtained at the previous inspection).

However, the posture and the size of the lung field of the patient (they change according to the amount of air accumulated within lungs when the patient temporarily stops breathing or the like) may be different between this inspection and the previous inspection. Accordingly, for example, when the image interpretation doctor allows to display a slice image showing the chest part of one series of slice images obtained at this inspection within the first area of the display screen by operating a predetermined key (e.g., cursor move key or the like), the slice image showing a different body part from the body part shown by the slice image displayed within the first may be displayed within the second area of the display screen.

Further, one series of slice images obtained in single imaging are typically a thousand and several hundreds to several thousands of images. Accordingly, significant effort and burden are taken to associate one slice image of the one series of slice images obtained at this inspection with one slice image of one series of slice images obtained at the previous inspection.

As a related technology, Japanese Patent Application Publication JP-A-8-294485 discloses an image display system with which the burden on the image interpreter for comparison interpretation and the time and cost taken for image interpretation can be reduced. This image display system is an image display system for displaying plural sets of three-dimensional images including plural tomographic images acquired by plural times of inspection based on at least one medical image imaging modality on an output device, including designating means for designating at least one pair of first tomographic images in nearly identical anatomical tomographic positions from the plural sets of three-dimensional images, tomographic image pair setting means for setting at least one pair of tomographic images in nearly identical anatomical tomographic positions from the plural sets of three-dimensional images based on a tomographic interval of at least three-dimensional image of the plural sets of three-dimensional images and position information between the pair of first tomographic images, and display controlling means for causing the output device to display the set at least one pair of tomographic images (page 2, FIG. 1). According to the image display system, the very difficult operation of aligning the anatomical tomographic positions can be performed by a simple operation, and the burden on the image interpreter doctor can be reduced.

Further, JP-A-8-294485 also discloses that, in the processing of designating the pair of tomographic images in nearly identical anatomical tomographic positions, the designation processing is automatically performed using feature quantities of the three-dimensional images (paragraphs 136-139 on page 15). Thereby, the need for the image interpreter to designate the pair of tomographic images in nearly identical anatomical tomographic positions can be eliminated.

Furthermore, JP-A-8-294485 also discloses that, when there is no tomographic image in the calculated z coordinate position due to successive display of pairs of tomographic images, the tomographic image nearest the tomographic surface is displayed (paragraphs 148-153 on pages 16-17). Moreover, JP-A-8-294485 also discloses that the subtraction image of the pair of tomographic images is displayed (paragraphs 177-181 on pages 19-20).

In the image display system disclosed in JP-A-8-294485, for automatic designation processing of pair of tomographic images in nearly identical anatomical tomographic positions using feature quantities of the three-dimensional images, three-dimensional correlation calculation or two-dimensional correlation calculation between three-dimensional images is used (paragraphs 136-139 on page 15). However, since the feature quantities of the three-dimensional correlation calculation or two-dimensional correlation calculation between three-dimensional images are very large, there is a problem that processing load is great and the processing time becomes longer. Further, when the posture and the size of the lung field of the patient are different between this inspection and the previous inspection, and when the lesion part becomes larger, the identical anatomical tomographic positions of the pair of tomographic images with the maximum correlation coefficient are not necessarily nearly identical.

DISCLOSURE OF THE INVENTION

Accordingly, in view of the above-mentioned points, a first object of the present invention is to provide an apparatus capable of easily displaying an axial image of a body part desired by a user from among one series of axial images acquired by imaging an object to be inspected with a modality of CT, MRI, or the like, and a program to be used in the apparatus. Further, a second object of the present invention is to provide an apparatus capable of causing a display unit to display at a high speed with high accuracy one slice image included in one series of slice images and another slice image included in another series of slice images showing a substantially same body part as the body part shown in the one slice image, and a program to be used in the apparatus.

In order to achieve the above-mentioned objects, a medical image display processing apparatus according to a first aspect of the present invention is an apparatus for causing a display unit to display an axial image based on image data representing one series of axial images obtained by imaging an object to be inspected, and the apparatus includes: part recognizing means for recognizing a body part shown in each of one series of axial images; and display processing means for causing the display unit to display an axial image included in the one series of axial images, and causing, when receiving a body part change instruction, the display unit to display an axial image showing a different body part from the body part of the axial image being displayed on the display unit based on a recognition result of the part recognizing means.

A medical image display processing program according to the first aspect of the present invention is a program, embodied on a computer readable medium, for causing a display unit to display an axial image based on image data representing one series of axial images obtained by imaging an object to be inspected, and the program actuates a CPU to execute the procedures of: (a) recognizing a body part shown in each of one series of axial images; (b) causing the display unit to display an axial image included in the one series of axial images; and (c) causing when receiving a body part change instruction, the display unit to display an axial image showing a different body part from the body part of the axial image being displayed on the display unit based on a recognition result at procedure (a).

A medical image display processing apparatus according to a second aspect of the present invention is an apparatus for causing a display unit to display an axial image based on image data representing plural series of axial images obtained by imaging an object to be inspected, and the apparatus includes: part recognizing means for recognizing a body part shown in each of plural series of axial images; and display processing means for causing the display unit to display an axial image included in one series of axial images, and causing the display unit to display an axial image included in another series of axial images showing a substantially same body part as the body part shown in the axial image being displayed on the display unit based on a recognition result of the part recognizing means.

A medical image display processing program according to the second aspect of the present invention is a program, embodied on a computer readable medium, for causing a display unit to display an axial image based on image data representing plural series of axial images obtained by imaging an object to be inspected, and the program actuating a CPU to execute the procedures of: (a) recognizing a body part shown in each of plural series of axial images; (b) causing the display unit to display an axial image included in one series of axial images; and (c) causing the display unit to display an axial image included in another series of axial images showing a substantially same body part as the body part shown in the axial image being displayed on the display unit based on a recognition result at procedure (a).

According to the first aspect of the present invention, part recognition is performed with respect to one series of axial images, and an axial image of a body part desired by a user can be displayed based on the recognition result. Thereby, the effort and burden on the user can be reduced. Further, according to the second aspect of the present invention, part recognition is performed with respect to plural series of axial images, and one slice image included in one series of slice images and another slice image included in another series of slice images showing a substantially same body part as the body part shown in the one slice image can be displayed on the display unit at a high speed with high accuracy based on the recognition result.

BEST MODE FOR CARRYING OUT THE INVENTION

Figure 1:
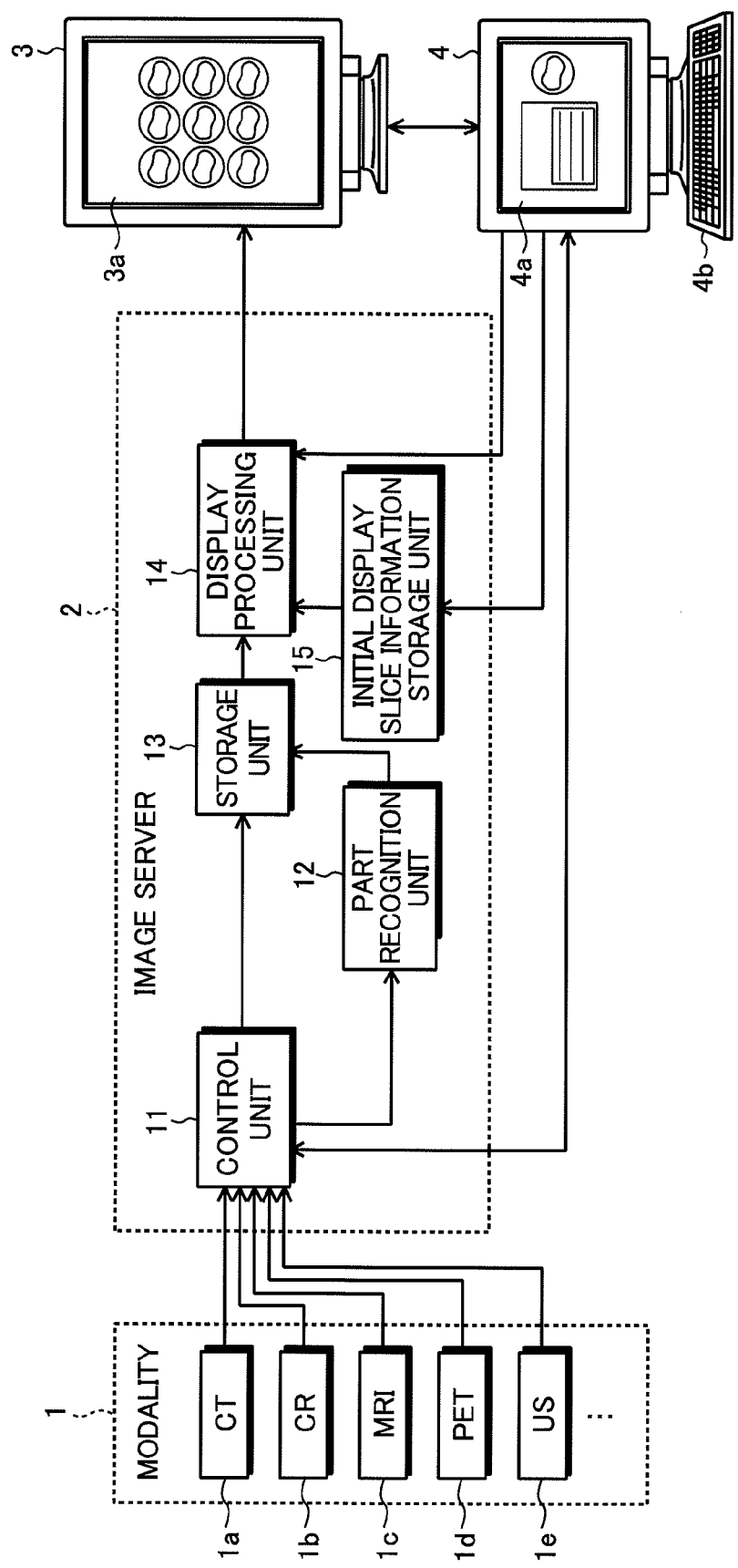
FIG. 1 shows a configuration of a medical image imaging system including a medical image display processing apparatus according to the first embodiment of the present invention.

Hereinafter, some embodiments of the present invention will be explained in detail by referring to the drawings. The same reference numerals are assigned to the same component elements and the explanation thereof will be omitted.

FIG. 1 is a block diagram showing a configuration of a medical image imaging system including a medical image display processing apparatus according to the first embodiment of the present invention. The medical image imaging system includes a modality 1 for performing imaging inspection of medical images on an object to be inspected, an image server 2 as the medical image display processing apparatus according to the first embodiment of the present invention, an image display terminal 3, and an image interpretation terminal 4. These devices 1-4 are compliant with the DICOM (Digital Imaging and Communications in Medicine) standard.

The modality 1 includes a medical image imaging apparatus such as a CT apparatus 1a, a CR (computed radiography) apparatus 1b, an MRI apparatus 1c, a PET apparatus 1d, and an ultrasonic diagnostic apparatus (US) 1e, and so on. These modalities 1a-1e generate image data by performing imaging inspection and output the data with image supplementary information to the image server 2.

The image server 2 is a PACS (Picture Archiving and Communication System) server for storing and managing image data acquired by the modality 1. The image server 2 outputs image data to the image display terminal 3 according to the request of the image interpretation terminal 4, which will be described later.

As shown in FIG. 1, the image server 2 has a control unit 11, a part recognition unit 12, a storage unit 13, a display processing unit 14, and an initial display slice information storage unit 15. The control unit 11, the part recognition unit 12, and the display processing unit 14 are configured by a CPU (central processing unit) and a medical image display processing program according to the embodiment, for example.

The control unit 11 causes the storage unit 13 to store the image data outputted from the modality 1. Further, the control unit 11 confirms the orientation of the images (axial, coronal, sagittal, or the like) represented by the inputted image data, and also outputs the image data to the part recognition unit 12 when the orientation is axial. The orientation of images is acquired from image supplementary information provided with DICOM tag (0020, 0037): Image Orientation (Patient) or (0020, 0020): Patient Orientation.

The part recognition unit 12 recognizes which part (body part) of the object is shown in each axial image based on plural axial images (hereinafter, also referred to as "slice images") represented by one series of image data. Then, the unit generates information (part information) including recognition results (parts), associates the information with the image data, and causes the storage unit 13 to store the data. The parts may be expressed by a character string of "Head", "Neck", "Chest", or the like, or expressed by an integral value that has been coded in advance of 1: head, 2: neck, 3: chest, or the like.

The storage unit 13 is, for example, a hard disk drive built in the image server 2, and stores image data and image supplementary information thereof, part information generated by the part recognition unit 12, control programs for operating the part recognition unit 12, and so on under control of the control unit 11. As the recording medium, not only the hard disk, but also an MO, an MT, a RAM, a CD-ROM, a DVD-ROM, or the like may be used. In this case, a drive unit for driving those recording media is built in the image server 2 or externally connected to the image server 2.

The display processing unit 14 receives display part indicating information for the user to indicate a desired part and display slice image indicating information for the user to indicate a desired slice image from the image interpretation terminal 4, and causes the image display terminal 3 to display a slice image of the part according to the display part indicating information and the display slice image indicating information from among the plural slice images represented by one series of image data.

The initial display slice information storage unit 15 stores initial display slice information for the display processing unit 14 to initially (e.g., when the user (image interpretation doctor) starts image interpretation by operating the image interpretation terminal 4) determine the slice image to be displayed on the image display terminal 3. The initial display slice information may be numbers (e.g., "1" which represents the first slice image of one series of axial images, or the like) or parts (e.g., "upper end of abdomen", or the like). When the initial display slice information is not stored in the initial display slice information storage unit 15, the display processing unit 14 may allow to display one axial image of the one series of axial images. The initial display slice information may be writable or updatable from the image interpretation terminal 4. Further, the storage unit 13 and the initial display slice information storage unit 15 may be realized by one recording medium.

The image display terminal 3 is a terminal device on which inspection images are displayed and has a high-definition display. Plural axial images are schematically shown on a screen 3a of the image display terminal 3 shown in FIG. 1.

The image interpretation terminal 4 is a device to be used by a user (image interpretation doctor) for generating image interpretation reports and so on while referring to inspection images displayed on the image display terminal 3, and includes a screen 4a for displaying image interpretation reports, an input device 4b such as a keyboard, and so on.

Next, the configuration and operation of the part recognition unit 12 shown in FIG. 1 will be explained with reference to FIGS. 2-4.

Figure 2:
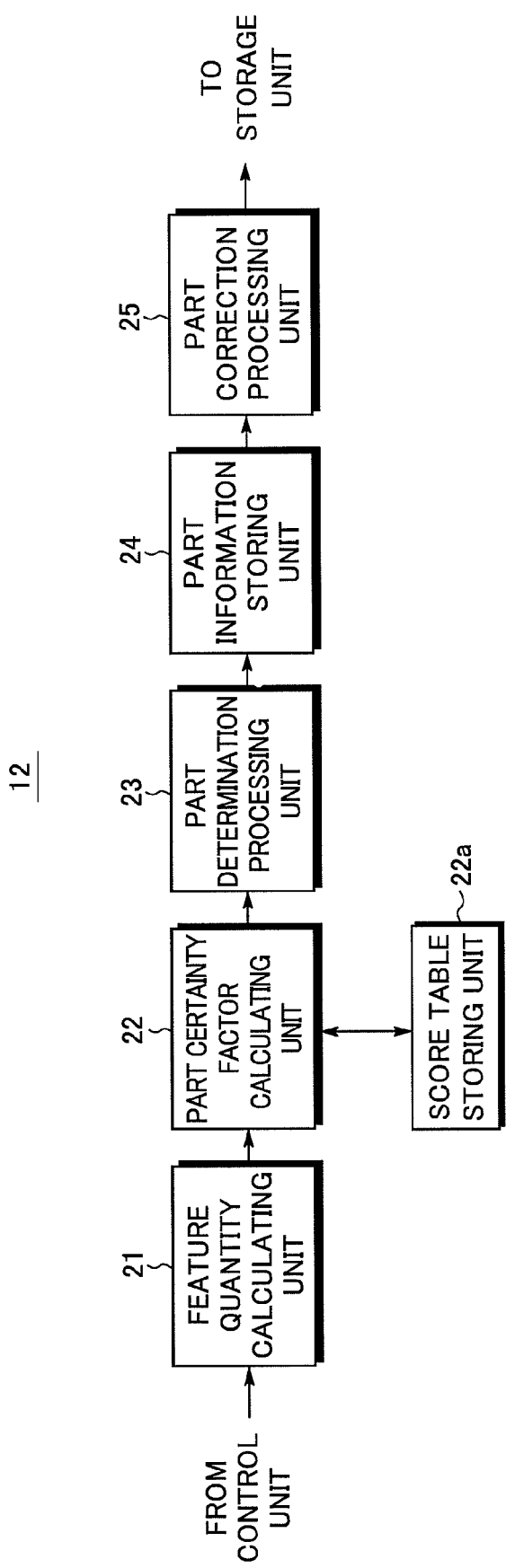
FIG. 2 is a block diagram showing functions of a part recognition unit shown in FIG. 1.

FIG. 2 is a block diagram showing functions of the part recognition unit 12 shown in FIG. 1. As shown in FIG. 2, the part recognition unit 12 includes a feature quantity calculating unit 21, a part certainty factor calculating unit 22, a score table storing unit 22a, a part determination processing unit 23, a part information storing unit 24, and a part correction processing unit 25. Among the units, the feature quantity calculating unit 21 to the part determination processing unit 23 operate to tentatively determine the part shown there for each slice image, and the part correction processing unit 25 operates to correct the part tentatively determined for each slice image based on part information of plural slice images. The part information of slice images will be described as below.

Figure 3:
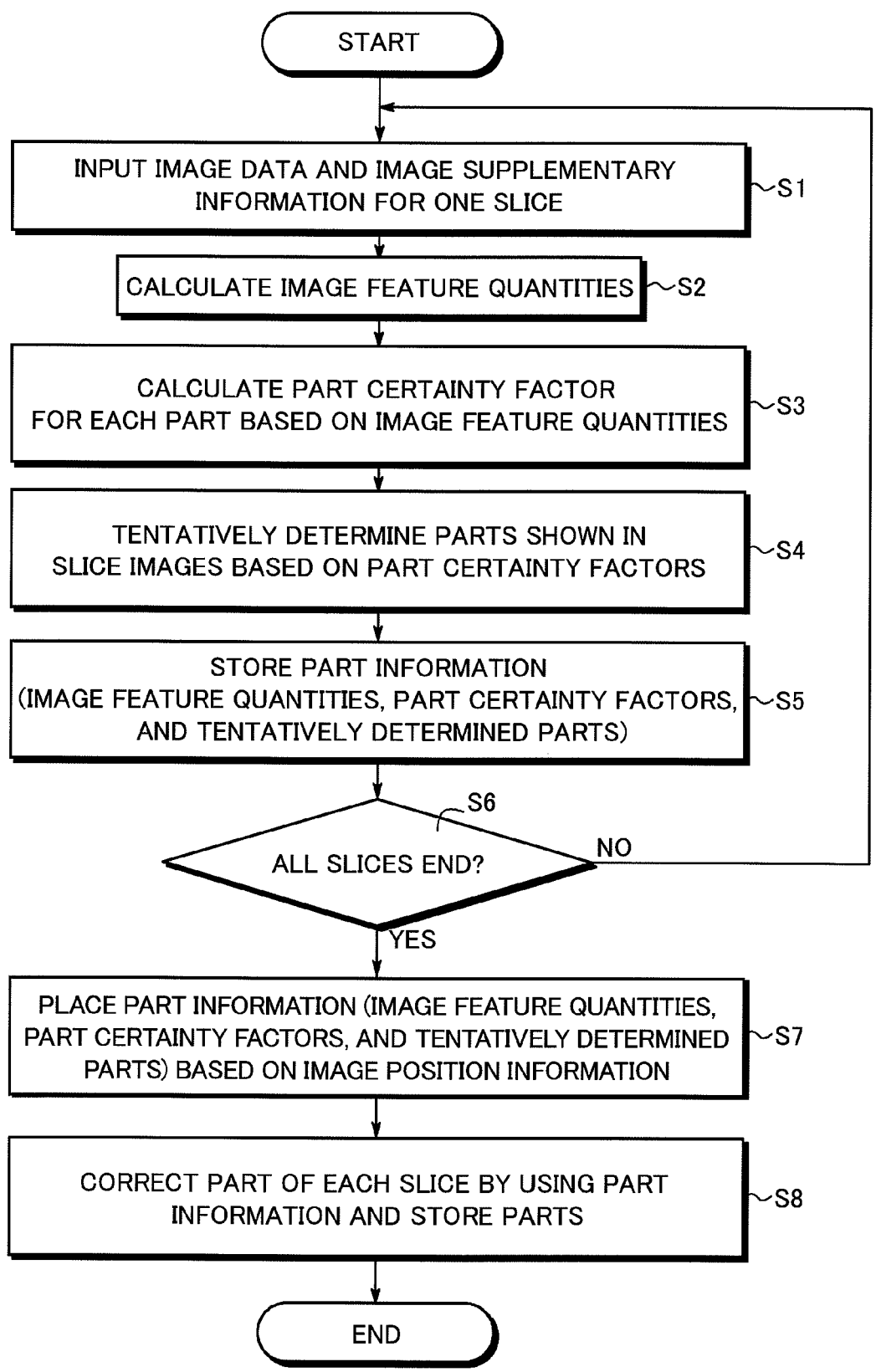
FIG. 3 is a flowchart showing an operation of the part recognition unit shown in FIG. 1.

FIG. 3 is a flowchart showing the operation of the part recognition unit 12. When the image data, which is determined to represent axial images by the control unit 11 (FIG. 1), is inputted to the part recognition unit 12, the part recognition operation as explained below is started.

At step S1, image data and image supplementary information thereof are inputted for each slice to the feature quantity calculating unit 21. Here, the image supplementary information includes information representing image orientation ((0020, 0037): Image Orientation (Patient) or (0020, 0020): Patient Orientation), information representing the spacing of pixels ((0028, 0030): Pixel Spacing), information representing the thickness of a slice ((0018, 0050): Slice Thickness), information representing the number of pixels included in one row or column ((0028, 0010): Rows and (0028, 0011): Columns), information representing the three-dimensional coordinates in the upper left position of an image ((0020, 0032): Image position (Patient)), and so on. Here, the contents in the parentheses express DICOM tags and attribute names of the respective information.

At step S2, the feature quantity calculating unit 21 calculates a feature quantity for one slice image. Here, the feature quantity is numeric conversion of the feature of the body part shown by the slice image. The feature quantity is calculated based on the shape of the body part shown in the slice image as shown in the following (A), for example. Further, when the value of each pixel data (i.e., pixel brightness) corresponds to the body part property (tissue property or the like), the feature quantity may be calculated according to the value as shown in the following (B) and (C). For example, the value of pixel data in a CT image is determined by a CT value, and the CT value is a physical quantity representing the amount of radiation transmitted through the body. The CT value of water is 0 HU, the CT value in the air region is about −1000 HU, and the CT value in the bone region is about 250 HU to 3000 HU.

(A) Degree of Circularity of Entire Body Part

The degree of circularity "ρ" is calculated by the following equation (1) by using the area "S" of a target region and the length "L" around the region.

$$\rho = 4\pi S/L^2 \tag{1}$$

The nearer a perfect circle the shape of the target region becomes, the closer to "1.0" the degree of circularity "ρ" becomes, and the farther from the perfect circle the shape becomes (e.g., the farther from "1" the ellipticity becomes), the smaller the degree becomes. For example, when the target region is the head, the degree of circularity is relatively high. Contrary, when the target region is the chest or abdomen, the degree of circularity is relatively low.

(B) Feature Quantity of Air Region: (Number of Pixels Having CT Values Representing Air Region)/(Number of Pixels of Entire Body Part)

For example, when the target region is the chest, the air region is relatively wide because of the existence of lungs. Contrary, when the target region is the head, the air region is nearly zero.

(C) Feature Quantity of Bone Region: (Number of Pixels Having CT Values Representing Bone Region)/(Number of Pixels of Entire Body Part)

For example, when the target region is the abdomen, the bone region relative to the entire body is a relatively small range. Contrary, when the target region is the leg, the bone region occupies the major part relative to the entire body.

Then, at step S3, the part certainty factor calculating unit 22 calculates apart certainty factor based on the feature quantity calculated by the feature quantity calculating unit 21. Here, the part certainty factor is numeric conversion of the likelihood that the target part is "certain part" (the likelihood of "head", the likelihood of "chest", or the like). In the embodiment, the part certainty factor is calculated by using a score table that has been prepared in advance.

Figures 4, 5:
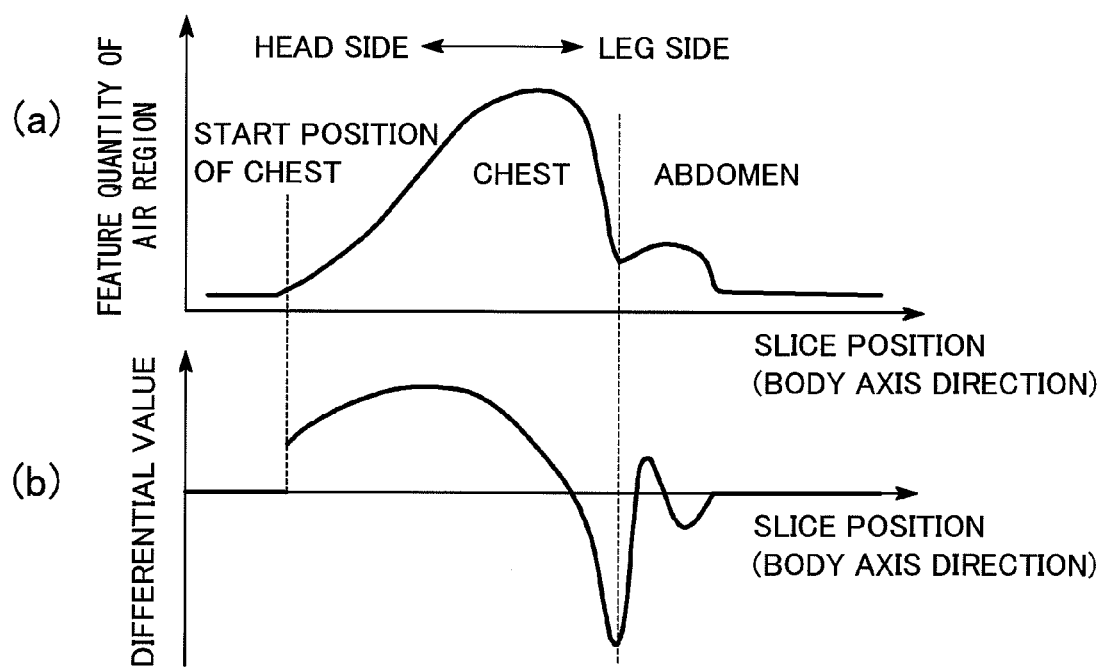
FIG. 4 shows a part certainty score table using feature quantities of air region.
FIG. 5 shows feature quantities of air region and differential values thereof.

FIG. 4 shows an example of score table to be used for calculation of part certainty factor. This score table is used when the likelihood of "head", the likelihood of "chest", the likelihood of "abdomen", and the likelihood of "leg" based on the value of the feature quantity of air region (the amount of air). In addition, "pelvis" may be used as a part item. Further, items (e.g., "head and neck part" or "chest and abdomen part") indicating the boundary between two adjacent parts (boundary region) or the region of a mixture of plural parts (mixture region, e.g., the head and neck or the chest and abdomen) may be used.

For example, when the feature quantity of air region of a body part shown by a CT image is 60%, by referring to the field of "40-80%" including 60% in the score table, it is found that the score of the likelihood of "head" of the body is "−1.0", the score of the likelihood of "chest" is "0.8", the score of the likelihood of "abdomen" is "−0.2", and the score of the likelihood of "leg" is "−1.0".

Such a score table is created for each feature quantity and stored in the score table storing unit 22a. The score table may be statistically created or intentionally created based on experiences of users (doctors or the like) or the like. The part certainty factor calculating unit 22 obtains the scores of the likelihood of each "part" with respect to each feature quantity by referring to the score table, and sums up the scores for each part. Thus obtained sum of scores with respect to each part is the part certainty factor.

With reference to FIG. 3 again, at step S4, the part determination processing unit 23 tentatively determines the part having the largest value of the part certainty factors obtained at step S3 as the part of the body shown in the slice image. When there are plural parts with larger values and the difference between them is within a predetermined range (e.g., within 10%), both parts may be adopted. For example, the part certainty factors of the chest and the abdomen are larger, the part of the slice is determined to be "chest" or "abdomen". Alternatively, when an item indicating a boundary region or a mixture region (e.g., "chest and abdomen part") is used, it may be adopted.

At step S5, the part information storing unit 24 stores the feature quantities obtained at step S2, the part certainty factors obtained at step S3, and the part tentatively determined at step S4 as part information (information on parts) of the slice images. All feature quantities are not necessarily stored, and only predetermined feature quantities (e.g., only the feature quantities obtained at step S8 described as below) may be stored.

The operation at steps S1-S5 is performed on all slice images included in one series (step S6). When the part information on all slice images are obtained, at step S7, the part correction processing unit 25 place the part information stored in the part information storing unit 24 in the order of slices. This is because the image data generated in the modality (FIG. 1) is not necessarily sent to the image server 2 in the order of slices. The order of slices is determined based on the image position information (0020, 0032): Image position (Patient) of the image supplementary information. Alternatively, instead of step S7, the part information storing unit 24 may store the part information while placing them in the order of slices based on the image position information at step S5.

Then, at step S8, the part correction processing unit 25 corrects the parts tentatively determined for each slice by using part information of the plural slice images. The correction methods are the following (1)-(3), for example.

(1) Method Using Part Information of Adjacent Slices

This method is a method of correcting the part tentatively determined for a slice image based on the positional relationship with adjacent slices.

The case where the tentatively determined part is "neck" in the 1st to 5th slices, "head" in the 6th slice, "neck" in the 7th to 10th slices, "chest" in the 11th to 15th slices, "leg" in the 16th slice, "chest" in the 17th to 20th slices, and "abdomen" in the 21st to 30th slices will be considered. In this case, since the part is "neck" in the preceding and subsequent slices of the 6th slice, the determination that the 6th slice is "head" is a recognition error, and correctly "neck". Further, since the part is "chest" in the preceding and subsequent slices of the 16th slice, the determination that the 16th slice is "leg" is a recognition error, and correctly "chest". In this way, when the part tentatively determined for a slice image is different from the part in the preceding and subsequent slice images, the part of the slice image is corrected by referring to the preceding and subsequent slice images.

(2) Method Using Feature Quantities

This method is a method of correcting the part tentatively determined for a slice image based on the change in feature quantity in the body axis direction.

FIG. 5(a) shows feature quantities of air region in the order of slice positions (in the body axis direction), and FIG. 5(b) shows differential values of feature quantities of air region. As shown in FIG. 5(b), from the observation of the change in feature quantity of air region from the upper section (head side) toward the lower section (leg side) of the object, it is found that there is a location where the feature quantity abruptly starts to increase. This location is set as the start position of the chest. Further, from the observation further toward the leg side, it is found that there is a location where the feature quantity changes from decrease to increase. The location is set as the boundary between the chest and the abdomen. When there is a slice image, which is tentatively determined as a part other than the chest, between the start position of the chest and the boundary between the chest and the abdomen, the part of the slice image is corrected to the chest.

(3) Method Utilizing Matching Curve

This method is a method of correcting the part tentatively determined for each slice image by referring to normal arrangement of parts in the object (e.g., human body).

Figure 6:
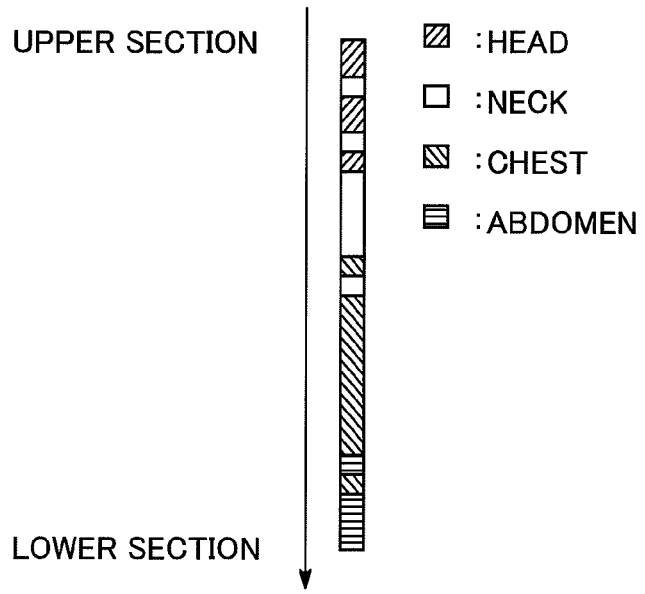
FIG. 6 is a diagram of tentatively determined parts (part recognition results) in the order of slices.

First, as shown in FIG. 6, the part tentatively determined for each slice image is placed in the order of slices from the upper section (head side) toward the lower section (leg side). As shown in FIG. 6, since the region where "Head" and "Neck" alternately appear and the region where "Neck" appears between "Chests" are seen in the part recognition result, it is considered that tentatively determined parts include many recognition errors.

Figure 7:
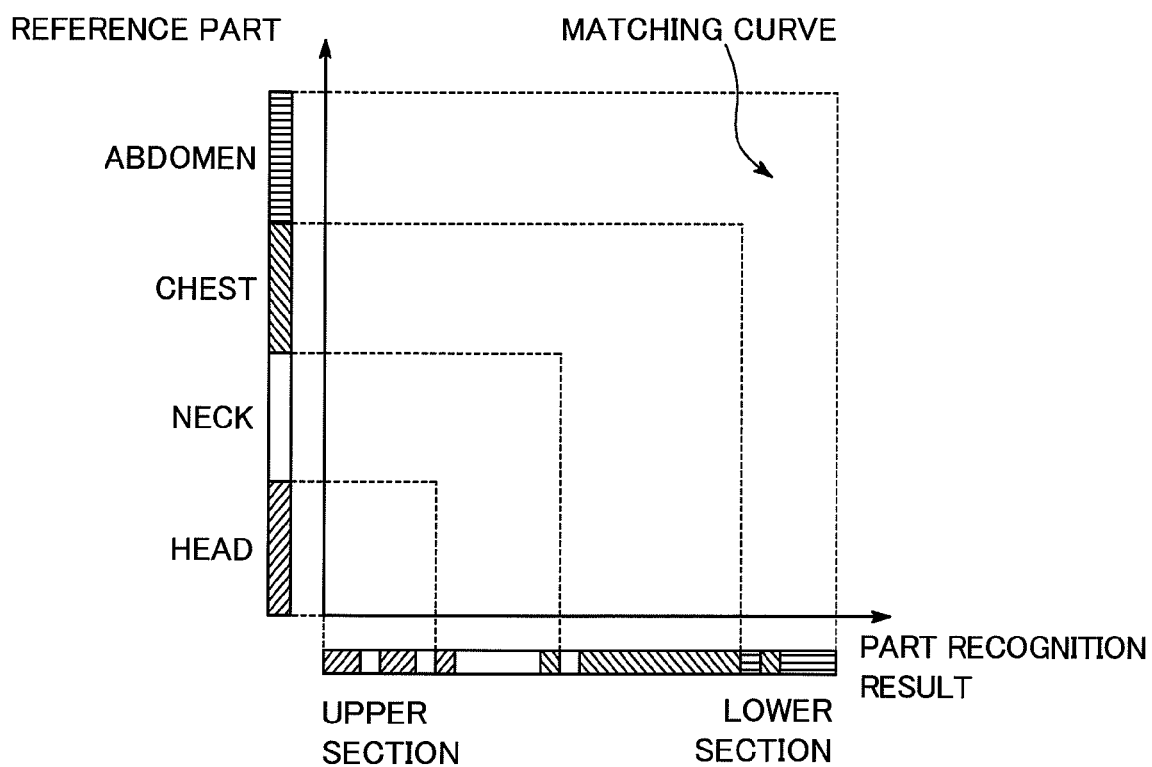
FIG. 7 shows a matching curve between the part recognition results and reference parts.

Then, as shown in FIG. 7, a matching curve between the part recognition results shown in FIG. 6 and the previously created reference parts is searched for. Here, since the parts of the human body are arranged in the order of head→neck→chest→abdomen, the reference parts arranged in such an order are created in advance as shown by the vertical axis in FIG. 7.

At the time of searching for the matching curve, given that the cost becomes higher when there is a mismatch between the part recognition result and the reference part, a curve that has the lowest cost is obtained. As a search method, various methods for solving the optimization problem are applicable. As below, a method of searching for a matching curve by using a dynamic programming method that is well known as one of the methods will be explained.

Figures 8, 9, 10:
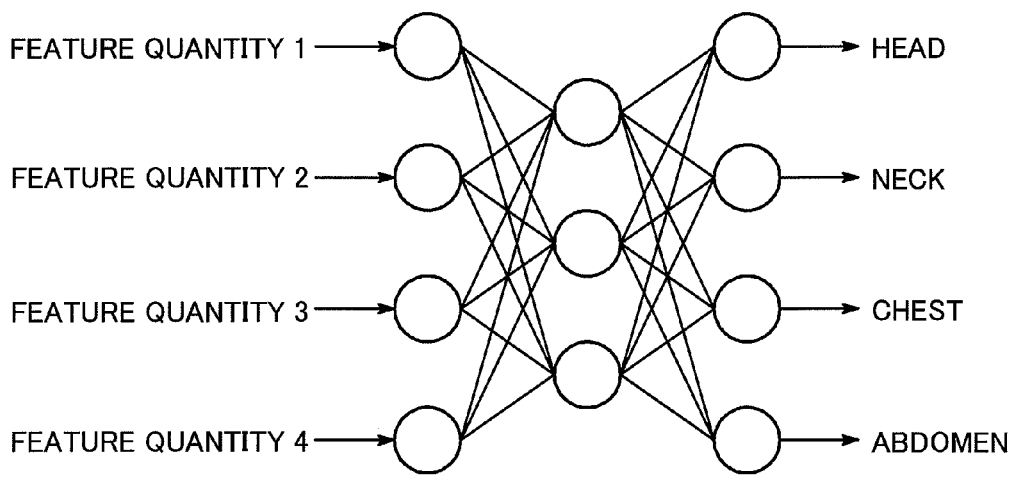
FIG. 8 is a weight map to be used for searching for a matching curve by using a dynamic programming method.
FIG. 9 is a cost map to be used for searching for a matching curve by using the dynamic programming method.
FIG. 10 is a diagram for explanation of a method of tentatively determining parts using the neural net.

First, a weight map as shown in FIG. 8 is created. In FIG. 8, the columns correspond to slice numbers and rows correspond to parts. In this weight map, the tentatively determined parts are set so that the weights are zero (areas enclosed by heavy lines). For example, with reference to FIG. 6, the first slice is tentatively determined as the head, and the value of the cell of the "Head" of the slice number "1" in the weight map is set to "0.0". Further, values of other cells are set larger than zero. Specifically, in the case where the certainty factor has been calculated for each slice image, the value of the difference between this certainty factor and the certainty factor of the tentatively determined part may be set, or a predetermined value other than the value may be set.

Then, a cost map as shown in FIG. 9 is created. In FIG. 9, the cost of each cell (n, m) is set as follows. Here, "n" indicates the slice number and "m" indicates the part number (1: Head, 2: Neck, 3: Chest, 4: Abdomen).

(1, 1): Value of (1, 1) in weight map (see FIG. 8)
(n, 1): Value of (n−1, 1) in weight map+Predetermined value
(1, m): Value of (1, m−1) in weight map+Predetermined value
(n, m): Minimum value among the following (i)-(iii)
(i) Value of (n−1, m−1) in cost map
 +Value of (n, m) in weight map
(ii) Value of (n, m−1) in cost map
 +Value of (n, m) in weight map+Predetermined value
(iii) Value of (n−1, m) in cost map
 +Value of (n, m) in weight map+Predetermined value Then, the surrounding minimum values are sequentially traced from right to left on the cost map. Thereby, a correspondence map of slice numbers to parts is created. As shown in FIG. 7, the correction of parts is performed by replacing the tentatively determined parts to corresponding parts in the reference parts based on the matching curve obtained as described above.

With reference to FIG. 3 again, at step S8, the part correction processing unit 25 outputs the corrected part information as image supplementary information to the storage unit 13 and causes the storage unit to store the information. The part information outputted from the part recognition unit 12 may be managed by an image information database, or written as tags in the image data that have been already stored in the storage unit 13.

As explained above, in the embodiment, after the part recognition is performed for each of the plural slice images included in one series, the part information of each slice is corrected by using the correlation of part information on plural slices. The advantage of performing part recognition through two stages is as follows. That is, part recognition processing can be started without waiting the input of all image data of one series to the server 2, and therefore, part recognition results can be obtained at a relatively high speed. Further, the part recognition result obtained for each slice is corrected based on the three-dimensional information of the object represented by the set of plural slice images, and therefore, major part recognition errors can be reduced. Thus, efficient and correct part recognition can be performed.

Here, in the embodiment, the part recognition unit 12 (FIG. 2) performs part recognition processing on all inputted slice images. However, DICOM tags may be referred to before the part recognition processing is started, and the part recognition processing may be performed only on the slice images without information representing the imaging part ((0018, 0015): Body Part). This is because the part may be added in the imaging stage.

Alternatively, the part recognition unit 12 may perform the part recognition processing while thinning the continuously inputted slice images at predetermined slice intervals. In this case, the entire processing can be made faster. Furthermore, the part recognition unit 12 may perform the part recognition processing only on a predetermined range of the continuously inputted slice images. For example, when the subject of diagnosis is the abdomen of the object, the start region of the abdomen (or the mixture region of the chest and abdomen) is needed to be recognized. In this case, the part recognition processing may be omitted for the range that is obviously considered as the leg from the information representing the three-dimensional coordinates of the slice image (DICOM tag (0020, 0032): Image position (Patient)), for example.

Further, in the embodiment, the score table is used when the part of the body shown on the slice is tentatively determined at steps S3 and S4, however, parts may be recognized utilizing a machine learning method such as the neural network instead.

Here, a method of tentatively determining the part utilizing the neural network will be explained.

As shown in FIG. 10, the feature quantities of the body part shown in the slice images (e.g., the feature quantities (A)-(C) explained at step S2) are inputted to the neural net. Then, the neural net is allowed to learn so that "1" is outputted for the part matching the part shown in the slice image and zero is outputted for other parts. For example, when the head is shown in the slice image, the output of "Head" is set to "1", and the outputs of "Neck", "Chest" and "Abdomen" are set to zero. Using thus learned neural network, the parts corresponding to the inputted feature quantities are acquired.

Further, in the embodiment, the part recognition unit 12 performs part recognition with respect to each of the plural slice images included in one series and then corrects the part information of the respective slices by using the correlation of part information on the plural slices, however, the unit may recognize the part by comparing a template image with the slice image (see the above-mentioned JP-P2002-253539A).

Next, an operation of the display processing unit 14 shown in FIG. 1 will be explained with reference to FIG. 11.

Figure 11:
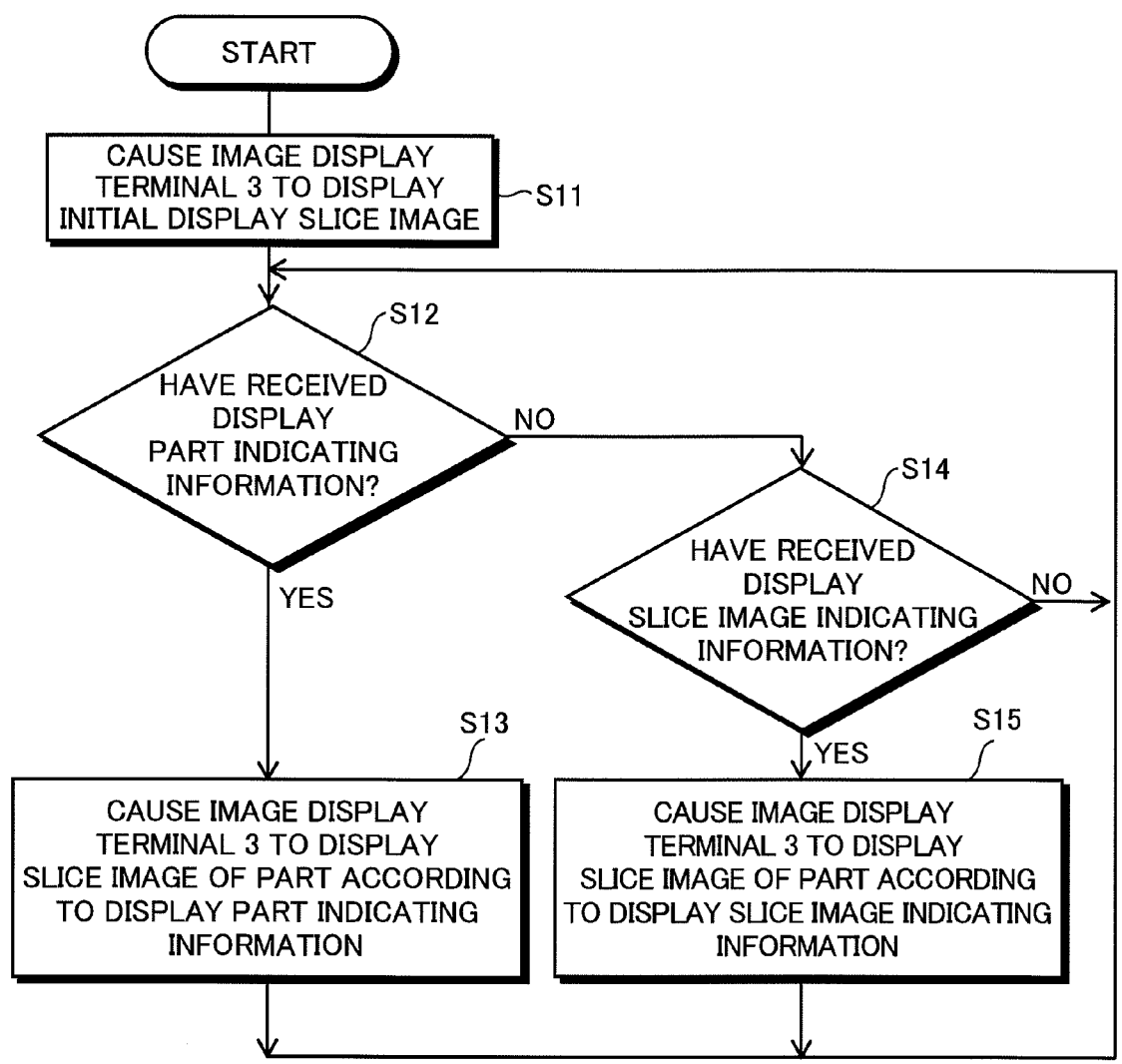
FIG. 11 is a flowchart showing an operation of a display processing unit shown in FIG. 1.

FIG. 11 is a flowchart showing the operation of the display processing unit 14 shown in FIG. 1.

At step S11, the display processing unit 14 loads the initial display slice information from the initial display slice information storage unit 15, loads the image data for displaying the slice image determined by the initial display slice information, and causes the image display terminal 3 to display the slice image based on the loaded image data.

At step S12, the display processing unit 14 checks whether the unit has received the display part indicating information from the image interpretation terminal 4 or not. If the unit has received the display part indicating information from the image interpretation terminal 4, the process moves to step S13, and if the unit has not received the display part indicating information from the image interpretation terminal 4, the process moves to step S14.

At step S13, the display processing unit 14 loads the image data for displaying the slice image of the part according to the display part indicating information from the storage unit 13, and causes the image display terminal 3 to display the slice image based on the loaded image data.

On the other hand, at step S14, the display processing unit 14 checks whether the unit has received the display slice indicating information from the image interpretation terminal 4 or not. If the unit has received the display slice indicating information from the image interpretation terminal 4, the process moves to step S15, and if the unit has not received the display slice indicating information from the image interpretation terminal 4, the process returns to step S12.

At step S15, the display processing unit 14 loads the image data for displaying the slice image according to the display slice indicating information from the storage unit 13, and causes the image display terminal 3 to display the slice image based on the loaded image data.

Next, the operation of the display processing unit 14 will be explained by taking a specific example. Here, the one series of image data stored in the storage unit 13 includes 1st to 20th image data. Further, the part recognition unit 12 has recognized parts such that the 1st to 10th image data are image data representing slice images of the chest part and the 11th to 20th image data are image data representing slice images of the abdomen part. Furthermore, the slice number "15" is stored as the initial display slice information in the initial display slice information storage unit 15.

In this case, initially, the display processing unit 14 loads the 15th image data (representing the slice image of the abdomen part) from the storage unit 13, and causes the image display terminal 3 to display the slice image based on the loaded image data (step S11).

Here, when the user (image interpretation doctor) presses down a predetermined first key (e.g., cursor upward move key ("↑" key or the like) (step S12), the display processing unit 14 loads the image data (here, the 10th image data) for displaying the slice image at the lower end of the chest part, which is an adjacent part to the upper part of the abdomen part as the part of the slice image being currently displayed, and causes the image display terminal 3 to display the slice image based on the loaded image data (step S13).

Then, when the user presses down a predetermined second key (e.g., cursor leftward move key ("←" key or the like) (step S14), the display processing unit 14 loads the image data (here, the 9th image data) for displaying the next slice image up to the slice image being currently displayed (based on the 10th image data), and causes the image display terminal 3 to display the slice image (the chest part) based on the loaded image data (step S15).

Then, when the user presses down a predetermined third key (e.g., cursor downward move key ("↓" key or the like) (step S12), the display processing unit 14 loads the image data (here, the 11th image data) for displaying the slice image at the upper end of the abdomen part, which is an adjacent part to the lower part of the chest part as the part of the slice image being currently displayed, and causes the image display terminal 3 to display the slice image (the abdomen part) based on the loaded image data (step S13).

Then, when the user presses down a predetermined fourth key (e.g., cursor rightward move key ("→" key or the like) (step S14), the display processing unit 14 loads the image data (here, the 12th image data) for displaying the next slice image down to the slice image being currently displayed (based on the 11th image data), and causes the image display terminal 3 to display the slice image (the abdomen part) based on the loaded image data (step S15).

As explained above, according to the embodiment, part recognition is performed with respect to each of the plural slice images included in one series, and the slice image of the part desired by the user (image interpretation doctor) can be displayed on the image display terminal 3 based on the part recognition result. Thereby, the burden on the user (image interpretation doctor) can be reduced.

The part recognition unit 12 may create identification information for identifying axial images showing the upper ends and/or lower ends of the respective parts. For example, when one series of image data stored in the storage unit 13 includes 1st to 20th image data, the 1st to 10th image data are image data representing slice images of the chest part and the 11th to 20th image data are image data representing slice images of the abdomen part, identification information for the part recognition unit 12 to identify that the 10th image data is image data representing the lower end of the chest part and the 11th image data is image data representing the upper end of the abdomen part may be created. This identification information may be added to the 10th and 11th image data as image supplementary information or tags, or may be stored in the stage unit 13 as data independent of the image data. If the identification information is created in this manner, loading of the 10th and 11th image data representing the slice images of the lower end of the chest part and the upper end of the abdomen part can be performed at a high speed.

In the embodiment, the part recognition unit 12 performs the part recognition processing on the image data inputted directly from the modality 1 to the image server 2. However, the part recognition processing may be performed by loading the image data that has been created in the modality 1 and then once stored in the recording medium. Further, part recognition processing may be performed when the display processing unit 14 displays the images on the image display terminal 3.

Next, a medical image display processing apparatus according to the second embodiment of the present invention will be explained.

Figure 12:
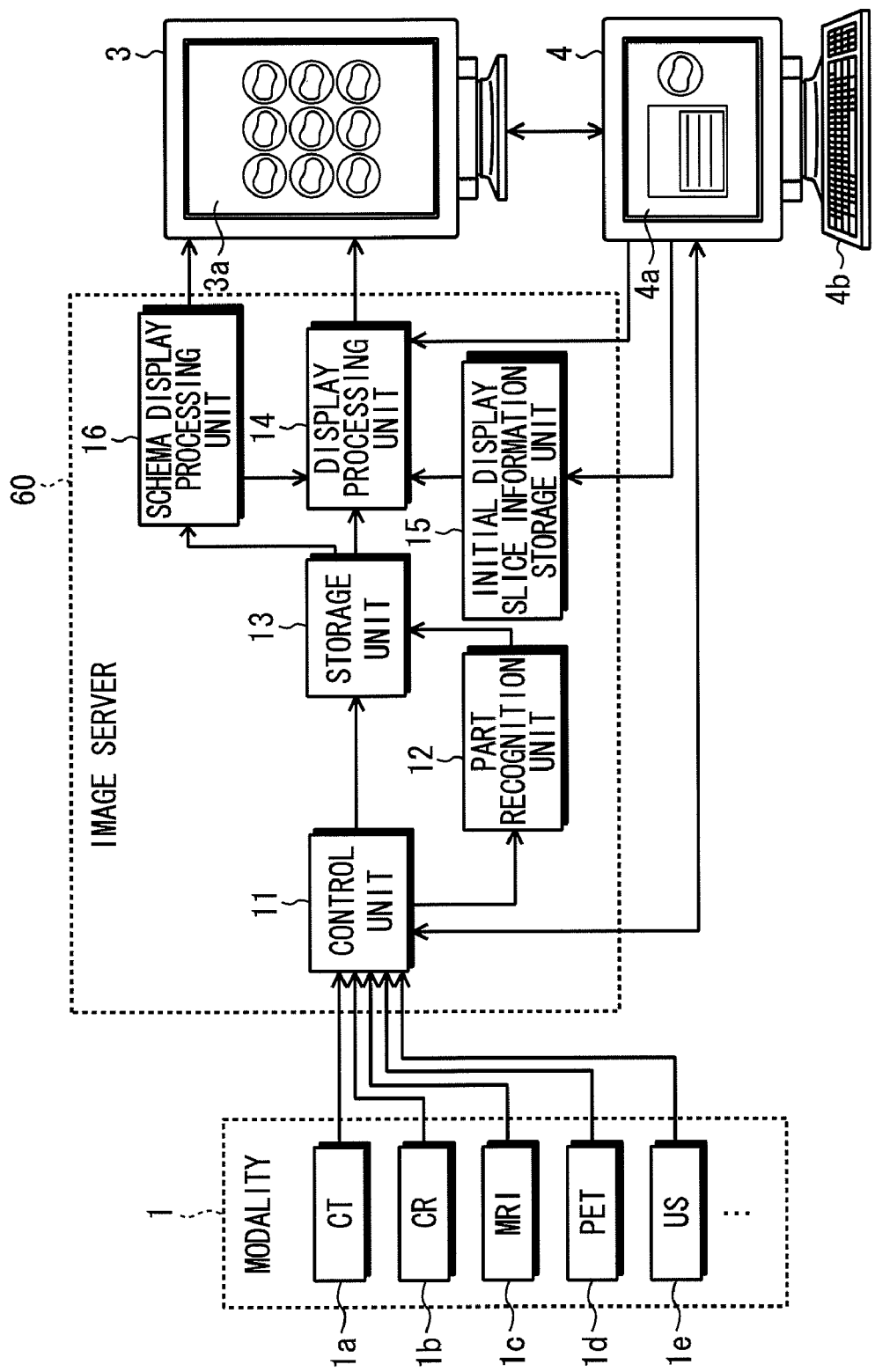
FIG. 12 shows a configuration of a medical image imaging system including a medical image display processing apparatus according to the second embodiment of the invention.

FIG. 12 is a block diagram showing a configuration of a medical image imaging system including the medical image display processing apparatus according to the embodiment. The medical image imaging system includes the modality 1, an image server 60 as the medical image display processing apparatus according to the second embodiment of the present invention, the image display terminal 3, and the image interpretation terminal 4. These devices 1, 3, 4, and 60 are compliant with the DICOM (Digital Imaging and Communications in Medicine) standard.

The image server 60 is a PACS server for storing and managing image data acquired by the modality 1. The image server 60 outputs image data to the image display terminal 3 according to the request of the image interpretation terminal 4, which will be described later.

As shown in FIG. 12, the image server 60 further has a schema display processing unit 16 in addition to the above explained control unit 11, part recognition unit 12, storage unit 13, display processing unit 14, and initial display slice information storage unit 15. The schema display processing unit 16 is configured by a CPU and a control program, for example.

The schema display processing unit 16 causes the image display terminal 3 to display a schema schematically showing a human body. The user (image interpretation doctor) can select a desired part in the schema displayed on the image display terminal 3.

Then, the operation of the display processing unit 14 and the schema display processing unit 16 shown in FIG. 12 will be explained with reference to FIG. 13.

Figure 13:
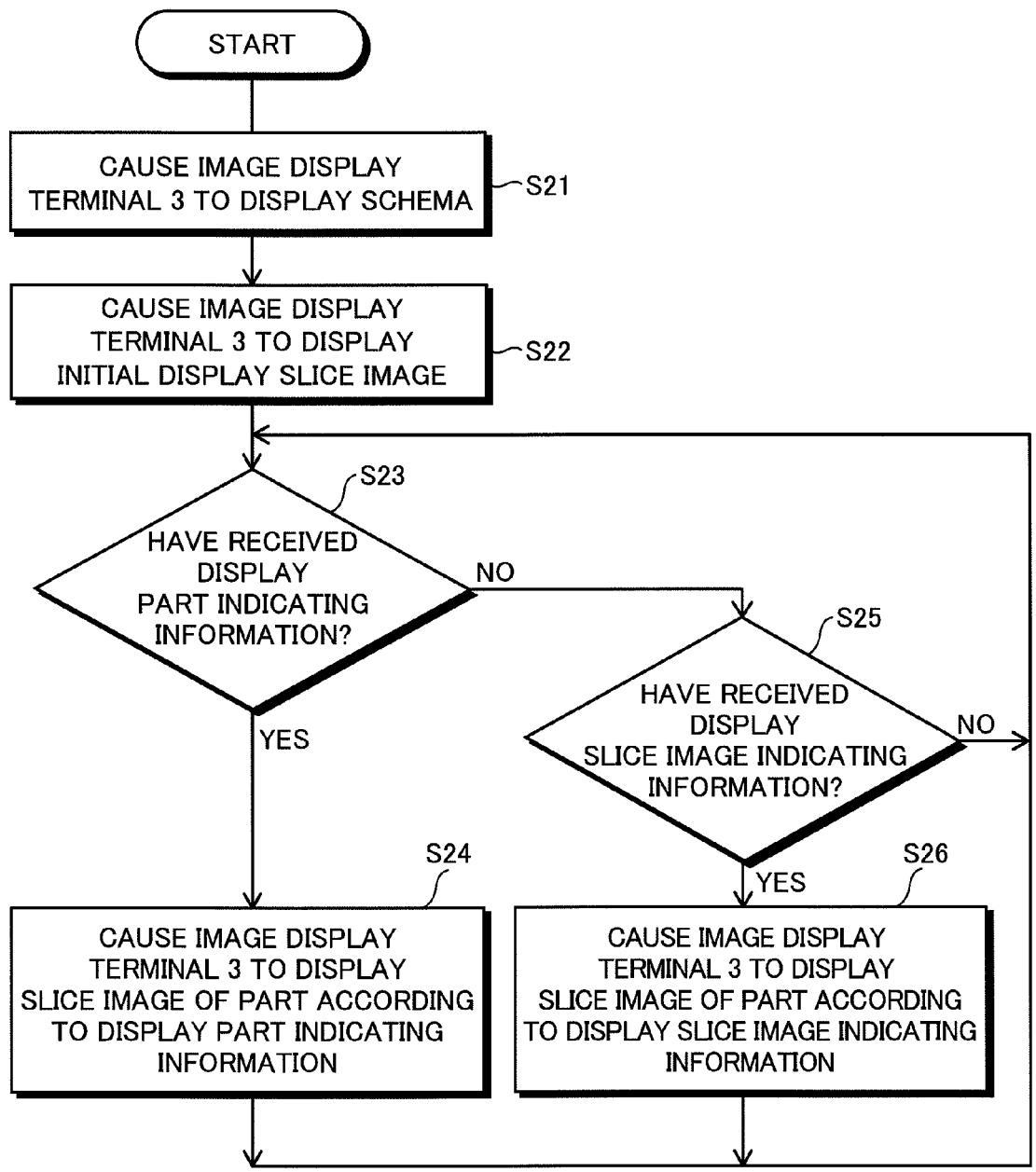
FIG. 13 is a flowchart showing an operation of a display processing unit and a schema display processing unit shown in FIG. 12.

FIG. 13 is a flowchart showing the operation of the display processing unit 14 and the schema display processing unit 16 shown in FIG. 12.

At step S21, the schema display processing unit 16 causes the image display terminal 3 to display the schema. At step S22, the display processing unit 14 loads the initial display slice information from the initial display slice information storage unit 15, loads the image data for displaying the slice image determined by the initial display slice information from the storage unit 13, and causes the image display terminal 3 to display the slice image based on the loaded image data.

At step S23, the display processing unit 14 checks whether or not the unit has received the display part indicating information from the image interpretation terminal 4. If the unit has received the display part indicating information from the image interpretation terminal 4, the process moves to step S24, and if the unit has not received the display part indicating information from the image interpretation terminal 4, the process moves to step S25.

At step S24, the display processing unit 14 loads the image data for displaying the slice image of the part according to the display part indicating information from the storage unit 13, and causes the image display terminal 3 to display the slice image based on the loaded image data.

On the other hand, at step S25, the display processing unit 14 checks whether the unit has received the display slice indicating information from the image interpretation terminal 4 or not. If the unit has received the display slice indicating information from the image interpretation terminal 4, the process moves to step S26, and if the unit has not received the display slice indicating information from the image interpretation terminal 4, the process returns to step S23.

At step S26, the display processing unit 14 loads the image data for displaying the slice image of the slice according to the display slice indicating information from the storage unit 13, and causes the image display terminal 3 to display the slice image based on the loaded image data.

Next, the operation of the display processing unit 14 and the schema display processing unit 16 will be explained by taking a specific example. Here, the one series of image data stored in the storage unit 13 includes 1st to 45th image data. Further, the part recognition unit 12 has recognized parts such that the 1st to 5th image data are image data representing slice images of the neck part, the 6th to 25th image data are image data representing slice images of the chest part, the 26th to 35th image data are image data representing slice images of the chest and abdomen part, and the 36th to 45th image data are image data representing slice images of the abdomen part. Furthermore, "the last slice image of the one series of slice images" (here, corresponding to the slice image (abdomen part) based on the 45th image data) is stored as the initial display slice information in the initial display slice information storage unit 15.

Figure 14:
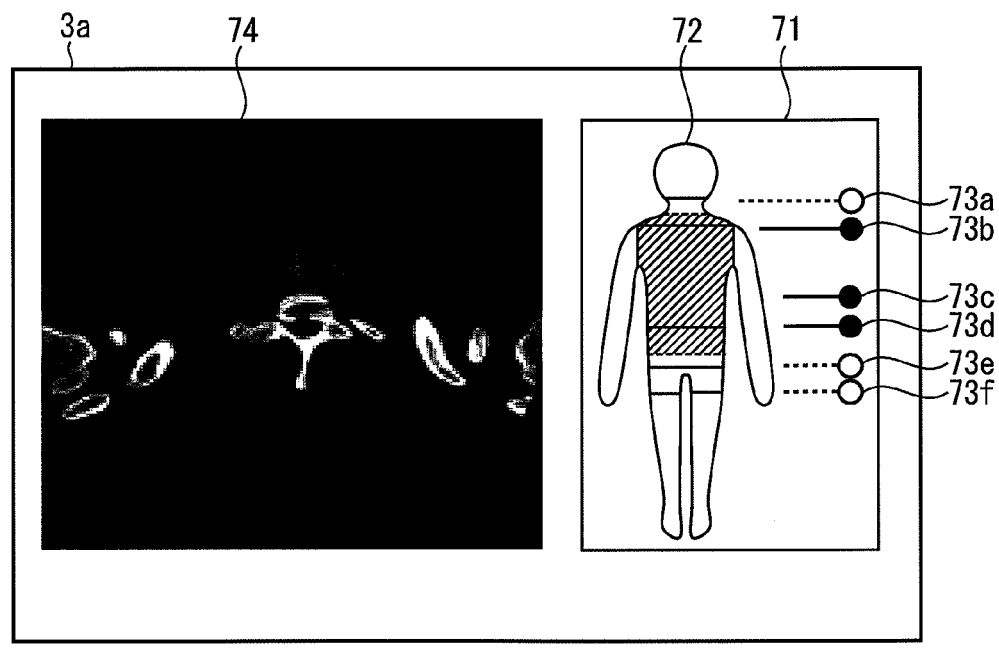
FIG. 14 shows an example of image displayed on an image display terminal shown in FIG. 12.

FIG. 14 shows an example of display screen of the image display terminal 3. As shown FIG. 14, a schema 72 is displayed within an area 71 of the display screen 3a of the image display terminal 3 (step S21). In the embodiment, since the part recognition has been made such that one series of image data stored in the storage unit 13 was obtained by imaging the neck part to the abdomen part of the object, the neck part to the abdomen part of the schema 72 are highlighted (here, hatched). Further, buttons 73a-73f are displayed on the right hand in the drawing of the boundary between the head part and the neck part, the boundary between the neck part and the chest part, the boundary between the chest part and the chest and abdomen part, the boundary between the chest and abdomen part and the abdomen part, the boundary between the abdomen part and the pelvis part, and the boundary between the pelvis part and the leg part of the schema 72, respectively. In the embodiment, the boundary between the neck part and the chest part, the boundary between the chest part and the chest and abdomen part, and the boundary between the chest and abdomen part and the abdomen part of the object are imaged, and accordingly, the buttons 73b-73d located on the right in the drawing are highlighted (blackened). On the other hand, in the embodiment, the boundary between the head part and the neck part, the boundary between the abdomen part and the pelvis part, and the boundary between the pelvis part and the leg part of the object are not imaged, and accordingly, the buttons 73a, 73e, and 73f are not highlighted.

Further, since "the last slice image of the one series of slice images" (here, corresponding to the slice image (abdomen part) based on the 45th image data) is stored as the initial display slice information in the initial display slice information storage unit 15, the slice image (abdomen part) based on the 45th image data is displayed within an area 74 of the display screen 3a of the image display terminal 3 (step S22).

Here, when the user (image interpretation doctor) clicks the button 73c (located on the right of the boundary between the chest part and the chest and abdomen part in the drawing) (step S23), the display processing unit 14 loads the image data (here, the 25th image data) for displaying the slice image at the lower end of the chest part from the storage unit 13, and causes the image display terminal 3 to display the slice image (chest part) based on the loaded image data within the area 74 of the display screen 3a (step S24).

Figure 15:
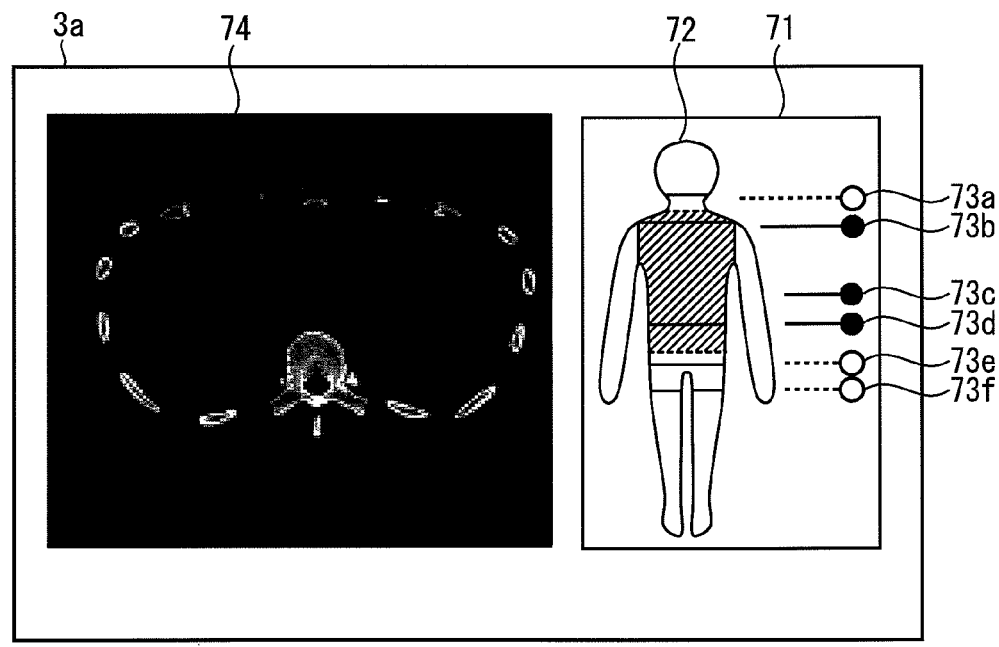
FIG. 15 shows an example of image displayed on the image display terminal shown in FIG. 12.

FIG. 15 shows the display screen 3a of the image display terminal 3 at this time. As shown in FIG. 15, the slice image (chest part) based on the 25th image data is displayed within the area 74 of the display screen 3a of the image display terminal 3. When the button 73c is clicked, the display processing unit 14 may load the image data (here, the 26th image data) for displaying the slice image at the upper end of the chest and abdomen part from the storage unit 13, and causes the image display terminal 3 to display the slice image (chest and abdomen part) based on the loaded image data within the area 74 of the display screen 3a.

Further, when the user clicks the button 73d (located on the right of the boundary between the chest and abdomen part and the abdomen part in the drawing) (step S23), the display processing unit 14 loads the image data (here, the 35th image data) for displaying the slice image at the lower end of the chest and abdomen part from the storage unit 13, and causes the image display terminal 3 to display the slice image (chest and abdomen part) based on the loaded image data within the area 74 of the display screen 3a (step S24).

Figure 16:
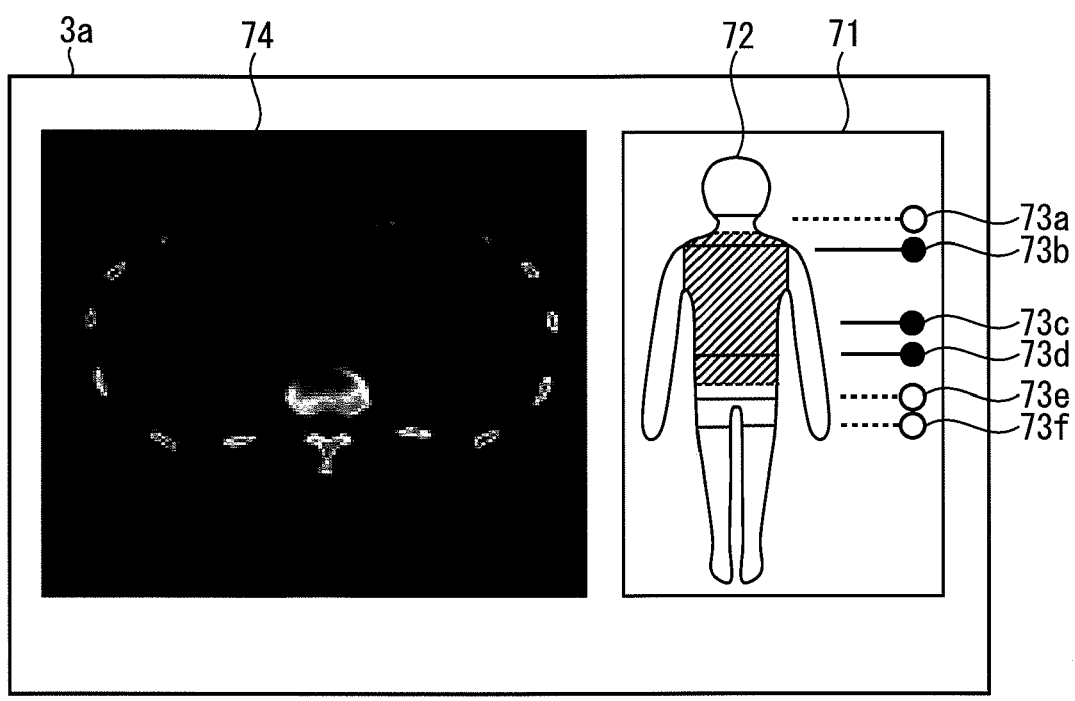
FIG. 16 shows an example of image displayed on the image display terminal shown in FIG. 12.

FIG. 16 shows the display screen 3a of the image display terminal 3 at this time. As shown in FIG. 16, the slice image (abdomen part) based on the 35th image data is displayed within the area 74 of the display screen 3a of the image display terminal 3. Note that, when the button 73d is clicked, the display processing unit 14 may load the image data (here, the 36th image data) for displaying the slice image at the upper end of the abdomen part from the storage unit 13, and causes the image display terminal 3 to display the slice image (abdomen part) based on the loaded image data within the area 74 of the display screen 3a. The operation when a predetermined key (e.g., cursor move key or the like) is pressed down is the same as that in the above explained first embodiment.

As explained above, according to the embodiment, the schema 72 can be displayed within the area 71 of the display screen 3*a* of the image display terminal 3, and the slice image showing the part selected by the user in the schema 72 can be displayed within the area 74 of the display screen 3*a* of the image display terminal 3. Thereby, the burden on the user (image interpretation doctor) can be reduced.

Next, a medical image display processing apparatus according to the third embodiment of the present invention will be explained. In the third embodiment, the display processing unit 14 shown in FIG. 1 causes the display unit to display at a high speed with high accuracy a slice image included in one series of slice images and a slice image included in another series of slice images showing nearly the same body part as the body part shown in that slice image. The rest is the same as that of the first embodiment.

The display processing unit 14 receives display slice image indicating information for indicating a slice image from the image interpretation terminal 4, and causes the image display terminal 3 to display the slice image according to the display slice image indicating information of one series of slice images (e.g., plural slice images obtained at this inspection) and causes the image display terminal 3 to display a slice image of another series of slice images (e.g., plural slice images obtained at the previous inspection) showing nearly the same body part as the body part shown in the slice image displayed on the image display terminal 3 according to the display slice image indicating information.

As below, the configuration and operation of the display processing unit in the medical image display processing apparatus according to the third embodiment will be explained with reference to FIGS. 17-20B.

In the following, two inspections are made for one patient at a time interval, and two series of slice images respectively obtained at two inspections are part-recognized by the part recognition unit 12 and stored in the storage unit 13. Further, one series of slice images obtained at the second inspection (this inspection) (hereinafter, referred to as "the first series of slice images") includes 1st to 25th image data, the part shown by the 1st to 10th slice images of these slice images is the chest part, the part shown by the 11th to 18th slice images is the abdomen part, and the part shown by the 19th to 25th slice images is the pelvis part. Furthermore, one series of slice images obtained at the first inspection (the previous inspection) (hereinafter, referred to as "the second series of slice images") includes 1st to 28th image data, the part shown by the 1st to 12th slice images of these slice images is the chest part, the part shown by the 13th to 21st slice images is the abdomen part, and the part shown by the 22nd to 28th slice images is the pelvis part.

Figure 17:
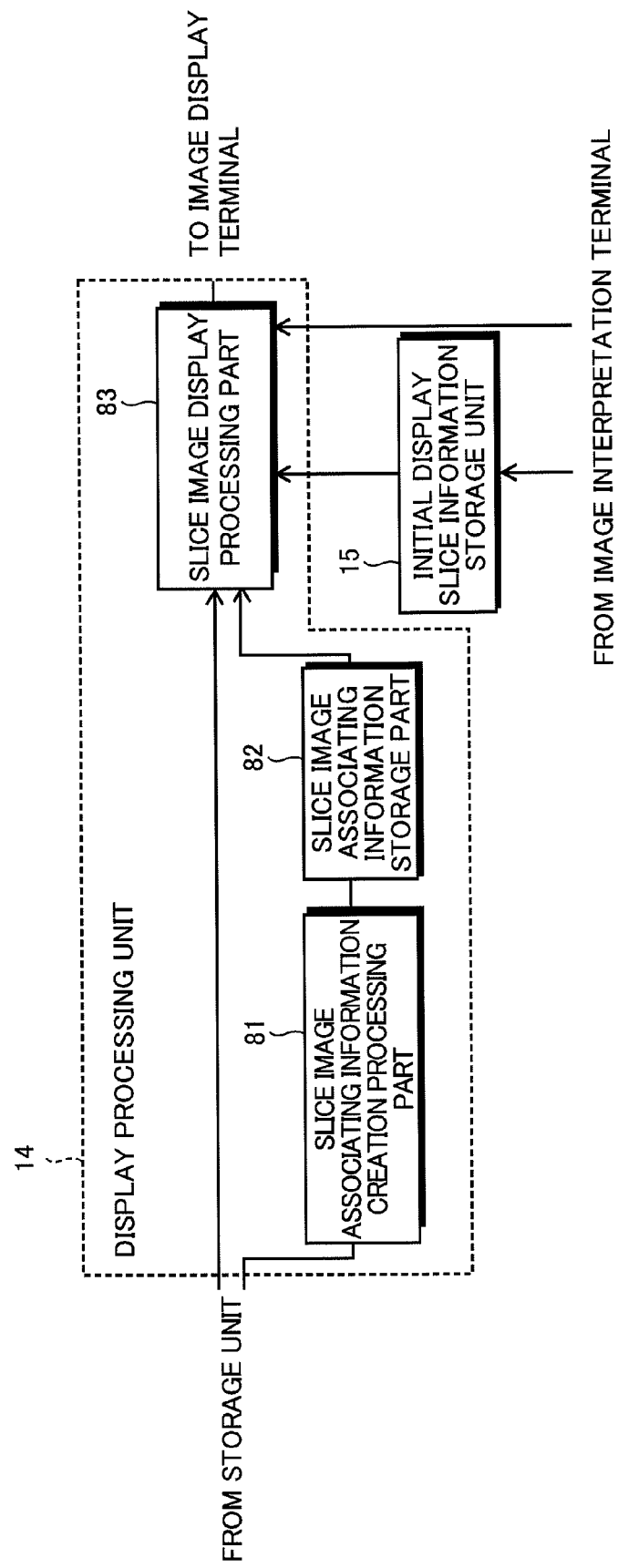
FIG. 17 is a block diagram showing a function of a display processing unit in a medical image display processing apparatus according to the third embodiment of the invention.

FIG. 17 is a block diagram showing a function of the display processing unit in the medical image display processing apparatus according to the third embodiment of the present invention. As shown in FIG. 17, the display processing unit 14 includes a slice image associating information creation processing part 81, a slice image associating information storage part 82, and a slice image display processing part 83.

The slice image associating information creation processing part 81 creates information associating the respective first series of slice images with the second series of slice images based on the part recognition result by the part recognition unit 12 and causes the slice image associating information storage part 82 to store the information.

The initial display slice information storage unit 15 stores initial display slice information for initially (e.g., when the user (image interpretation doctor) starts image interpretation by operating the image interpretation terminal 4) determining one slice image of the first series of slice images to be displayed on the image display terminal 3. The initial display slice information may be slice numbers (e.g., "1" (indicating the first slice image of the first series of axial images) or the like) or parts (e.g., "upper end of abdomen part" or the like). When the initial display slice information is not stored in the initial display slice information storage unit 15, the slice image display processing part 83 may allow to display one axial image of the first series of axial images. The initial display slice information may be writable or updatable from the image interpretation terminal 4. Further, the storage unit 13(FIG. 1), the slice image associating information storage part 82, and the initial display slice information storage unit 15 may be realized by one recording medium.

The slice image display processing part 83 receives display slice image indicating information for the user (image interpretation doctor) to indicate a desired slice image from the image interpretation terminal 4, and causes the image display terminal 3 to display the slice image according to the display slice image indicating information of the first series of slice images and causes the image display terminal 3 to display the slice image associated with the slice image displayed on the image display terminal according to the display slice image indicating information of the second series of slice images.

Figure 18:
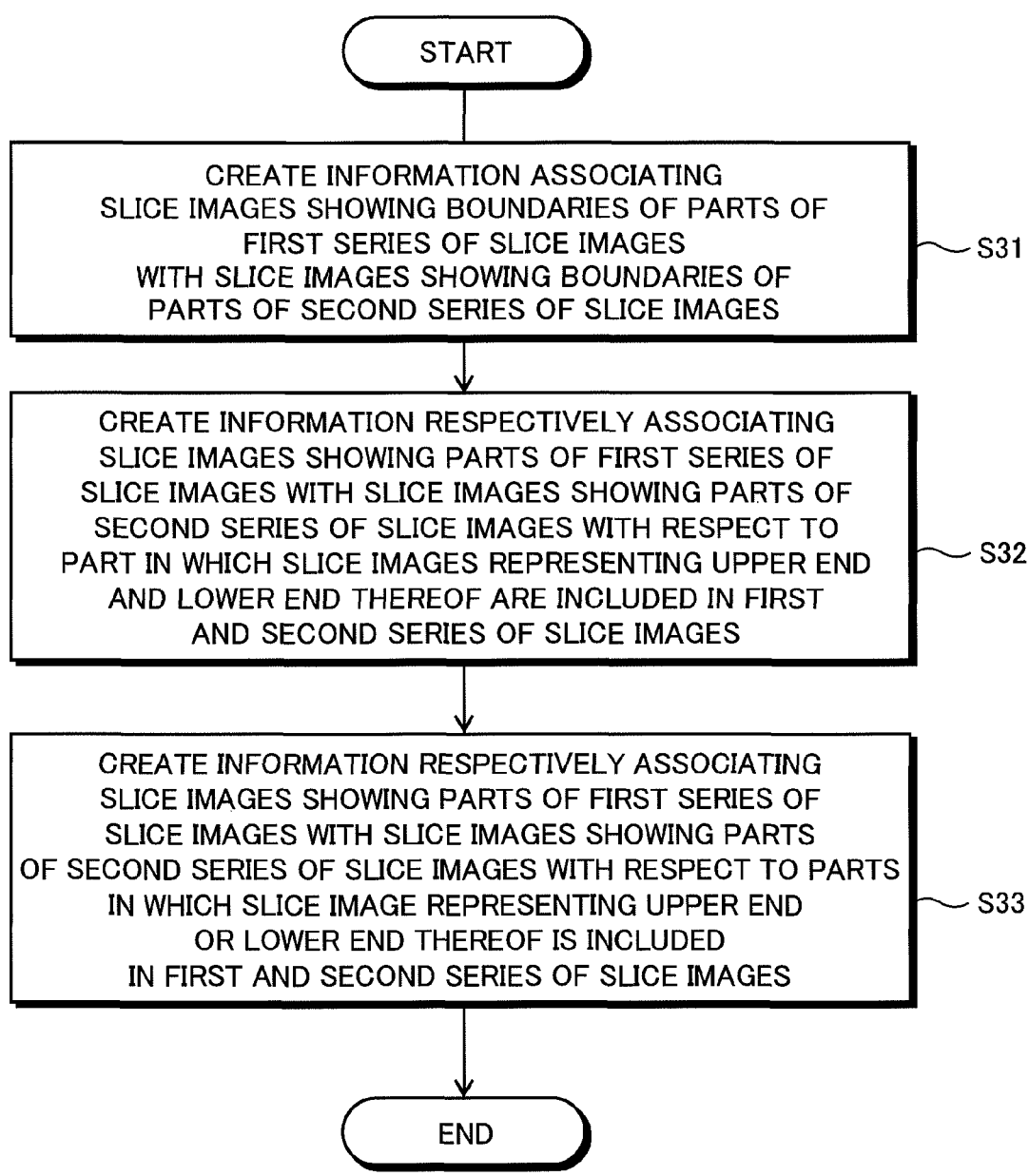
FIG. 18 is a flowchart of an operation of a slice image associating information creation processing part shown in FIG. 17.

FIG. 18 is a flowchart of an operation of the slice image associating information creation processing part shown in FIG. 17.

At step S31, the slice image associating information creation processing part 81 creates information associating the slice images showing boundaries of the parts of the first series of slice images with the slice images showing boundaries of the parts of the second series of slice images, respectively, and causes the slice image associating information storage part 82 to store the information. Here, the slice image associating information creation processing part 81 creates information associating the 10th slice image (showing the lower end of the chest part) of the first series of slice images with the 12th slice image (showing the lower end of the chest part) of the second series of slice images, and associating the 11th slice image (showing the upper end of the abdomen part) of the first series of slice images with the 13th slice image (showing the upper end of the abdomen part) of the second series of slice images, and causes the slice image associating information storage part 82 to store the information. Further, the slice image associating information creation processing part 81 creates information associating the 18th slice image (showing the lower end of the abdomen part) of the first series of slice images with the 21st slice image (showing the lower end of the abdomen part) of the second series of slice images, and associating the 19th slice image (showing the upper end of the pelvis part) of the first series of slice images with the 22nd slice image (showing the upper end of the pelvis part) of the second series of slice images, and causes the slice image associating information storage part 82 to store the information.

At step S32, with respect to the part in which slice images representing the upper end and lower end thereof are included in the first and second series of slice images, the slice image associating information creation processing part 81 creates information associating the slice images showing the part (except for the upper end and lower end) in the first series of slice images with the slice images showing the part (except for the upper end and lower end) in the second series of slice images, respectively, and causes the slice image associating information storage part 82 to store the information. Here, the slice images representing the upper end and lower end of the abdomen part are included in the first and second series of slice images, and accordingly, the slice image associating information creation processing part 81 creates information associating the 12th to 17th slice images showing the abdomen part (except for the upper end and lower end) in the first series of slice images with the 14th to 20th slice images showing the abdomen part (except for the upper end and lower end) in the second series of slice images, respectively, and causes the slice image associating information storage part 82 to store the information.

In this case, the number of slice images showing the abdomen part (except for the upper end and lower end) in the first series of slice images (total six of 12th to 17th slice images) is different from the number of slice images showing the abdomen part (except for the upper end and lower end) in the second series of slice images (total seven of 14th to 20th slice images). In such a case, each of the 12th to 17th slice images in the first series may be associated with respective one of slice images in the second series such that the ratio of the number of slices between the 13th slice image of the second series (showing the upper end of the abdomen part) and itself to the number of slices between the 21st slice image of the second series (showing the lower end of the abdomen part) and itself is the nearest the ratio of the number of slices between each of the respective 12th to 17th slice images in the first series and the 11th slice image in the first series (showing the upper end of the abdomen part) to the number of slices between each of the 12th to 17th slice images in the first series and the 18th slice image in the first series (showing the lower end of the abdomen part).

At step S33, with respect to the part in which the slice image representing the upper end or lower end thereof is included in the first and second series of slice images, the slice image associating information creation processing part 81 creates information associating the slice images showing the part of the first series of slice images (except for the upper end or lower end) with the slice images showing the part of the second series of slice images (except for the upper end or lower end), respectively, and causes the slice image associating information storage part 82 to store the information. Here, the slice image showing the lower end of the chest part is included in the first and second series of slice images, and accordingly, the slice image associating information creation processing part 81 creates information associating the 1st to 9th slice images showing the chest part (except for the lower end) in the first series of slice images with the 3rd to 11th slice images showing above nearest the lower end of the chest part (except for the lower end) in the second series of slice images, respectively, and causes the slice image associating information storage part 82 to store the information. Further, the slice image showing the upper end of the pelvis part is included in the first and second series of slice images, and accordingly, the slice image associating information creation processing part 81 creates information associating the 20th to 25th slice images showing the pelvis part (except for the upper end) in the first series of slice images with the 23rd to 28th slice images showing the pelvis part (except for the lower end) in the second series of slice images, respectively, and causes the slice image associating information storage part 82 to store the information.

Figure 19:
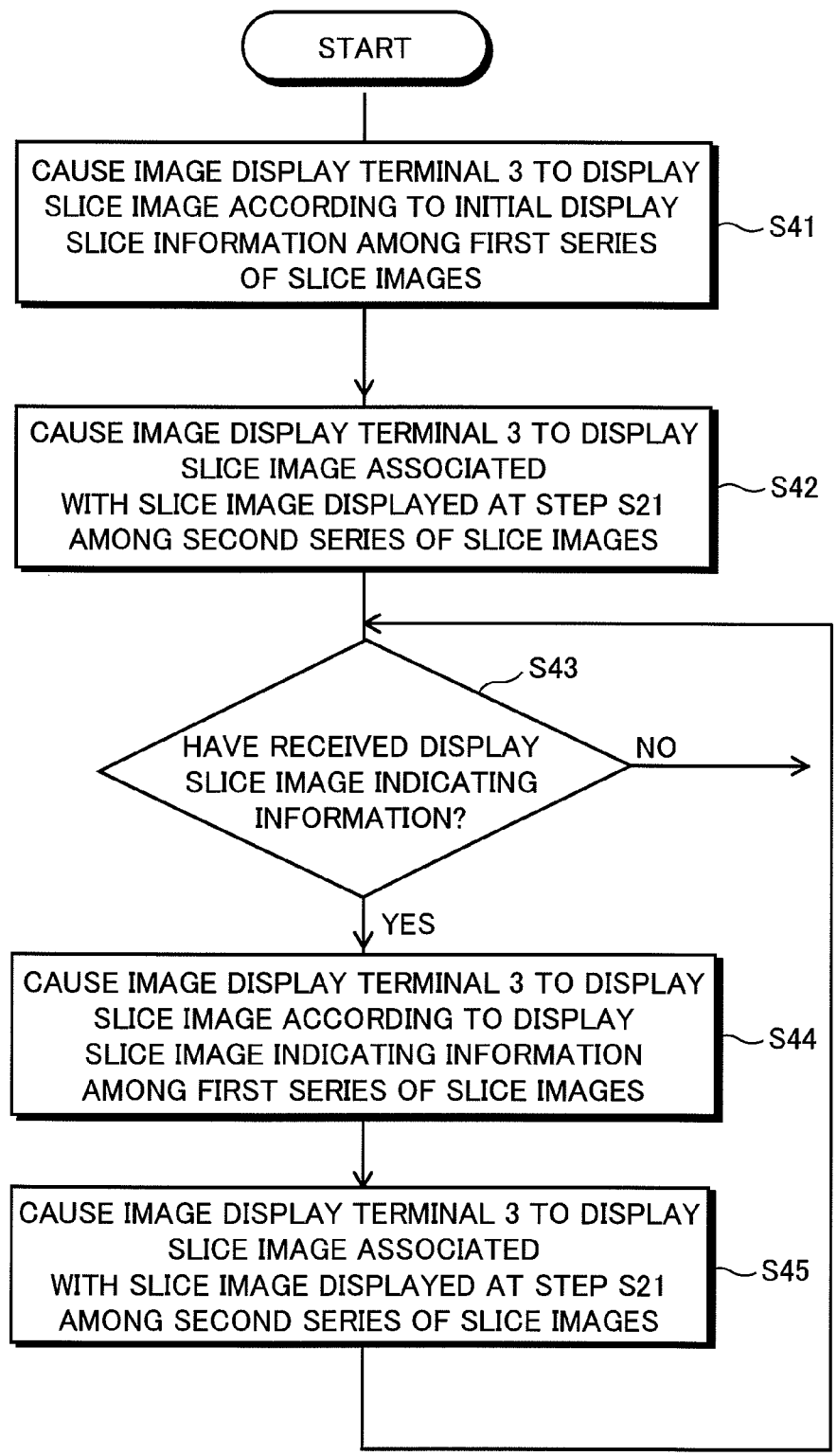
FIG. 19 is a flowchart showing an operation of a slice image display processing part shown in FIG. 17.

FIG. 19 is a flowchart showing an operation of the slice image display processing part shown in FIG. 17.

At step S41, the slice image display processing part 83 loads the initial display slice information from the initial display slice information storage unit 15, loads the image data for displaying the slice image determined by the initial display slice information of the first series of slice images from the storage unit 13, and causes the image display terminal 3 to display the slice image based on the loaded image data within the first area of the display screen 3a.

At step S42, the slice image display processing part 83 loads the image data for displaying the slice image associated with the slice image displayed at step S41 from the storage unit 13 with reference to the slice image associating information stored in the slice image associating information storage part 82, and causes the image display terminal 3 to display the slice image based on the loaded image data within the second area of the display screen 3a.

At step S43, the slice image display processing part 83 checks whether or not the display slice indicating information has been received from the image interpretation terminal 4. If the display slice indicating information has been received from the image interpretation terminal 4, the process moves to step S44.

At step S44, the slice image display processing part 83 loads the image data for displaying the slice image according to the display slice indicating information in the first series of slice images from the storage unit 13, and causes the image display terminal 3 to display the slice image based on the loaded image data within the first area 71 of the display screen 3a.

At step S45, the slice image display processing part 83 refers to the slice image associating information stored in the slice image associating information storage part 82, and loads the image data for displaying the slice image associated with the slice image displayed at step S44 in the second series of slice images from the storage unit 13, and causes the image display terminal 3 to display the slice image based on the loaded image data within the second area 72 of the display screen 3a. The process returns to step S43.

Next, the operation of the slice image display processing part 83 will be explained by taking a specific example. Here, "the last slice image of the one series of slice images" (here, corresponding to the slice image (abdomen part) based on the 25th image data) is stored as the initial display slice information in the initial display slice information storage unit 15.

Figure 20A:
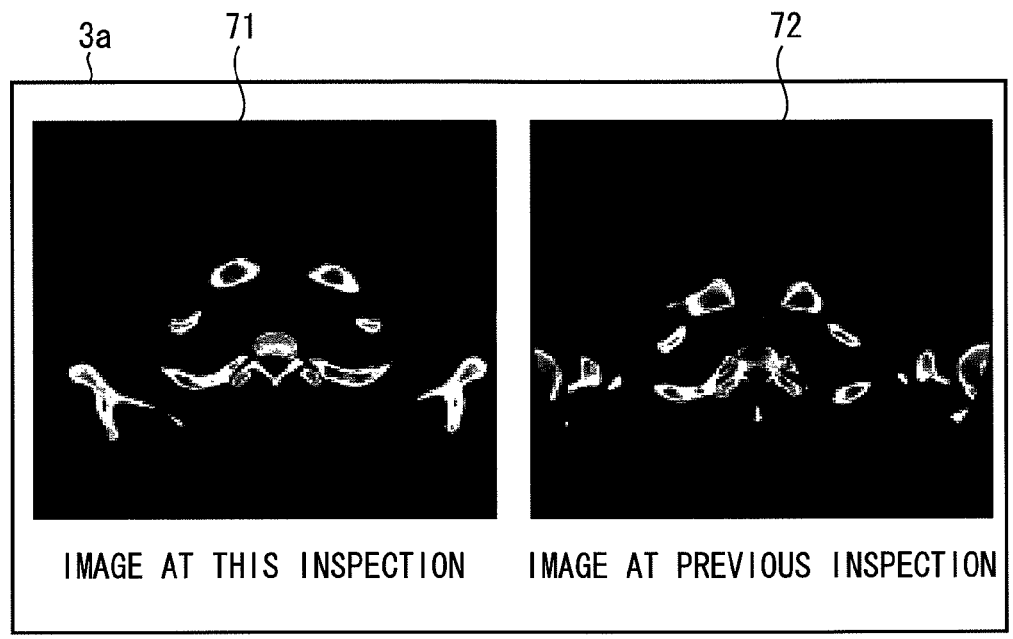
FIG. 20A shows an example of image displayed on the image display terminal.

FIG. 20A shows an example of display screen 3a of the image display terminal 3 shown in FIG. 1. As shown in FIG. 20A, the slice image (here, the 25th slice image) determined based on the initial display slice information of the first series of slice images is displayed within the area 71 of the display screen 3a of the image display terminal 3 (step S41), and the slice image (here, the 28th slice image) associated with the slice image displayed within the area 71 (the 25th slice image of the first series of slice images) in the second series of slice images is displayed within the area 72 of the display screen 3a of the image display terminal 3 (step S42).

Figure 20B:
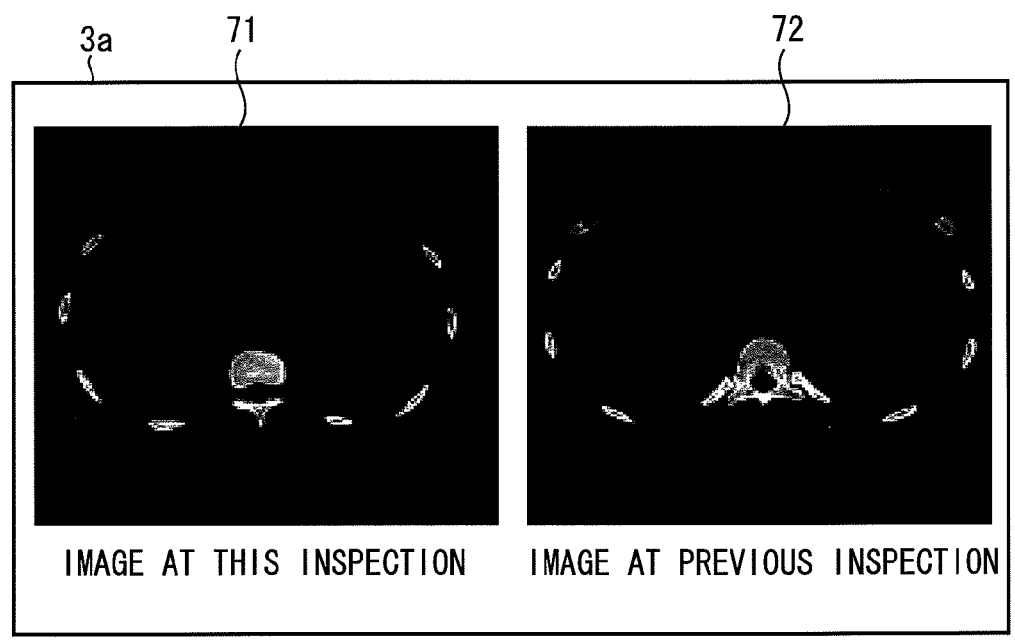
FIG. 20B shows an example of image displayed on the image display terminal.

Here, when the image interpretation doctor operates a predetermined key (e.g., cursor move key or the like) of the image interpretation terminal 4 (step S43), as shown in FIG. 20B, the slice image showing the chest part of the first series of slice images (e.g., the 10th slice image) can be displayed within the area 71 (step S44). Further, within the area 72, the slice image (here, the 12th slice image) associated with the slice image displayed within the area 71 (here, the 10th slice image of the first series of slice images) of the second series of slice images is displayed (step S45).

As explained above, according to the embodiment, part recognition is performed with respect to each of the plural slice images included in two series, and the slice included in the first series of slice images and the slice image included in the second series of slice images showing nearly the same body part as the body part shown in that slice image can be displayed on the image display terminal 3 based on the part recognition result. Therefore, the display of the slice included in the first series of slice images and the slice image included in the second series of slice images showing nearly the same body part as the body part shown in that slice image on the image display terminal 3 can be performed at a high speed. Further, the slice image included in the second series of slice images showing nearly the same body part as the body part shown in the slice image included in the first series of slice images can be determined with high accuracy.

In the embodiment, the part recognition unit 12 performs the part recognition processing on the image data inputted directly from the modality 1 to the image server 2. However, the part recognition processing may be performed by loading the image data that has been created in the modality 1 and then once stored in the recording medium. Further, part recognition processing and slice image associating processing may be performed when the display processing unit 14 displays the images on the image display terminal 3.

Further, in the embodiment, the slice image included in one series of slice images and the slice image included in another series of slice images showing nearly the same body part as the body part shown in that slice image are displayed side by side, however, a subtraction image of the slice image included in one series of slice images and the slice image included in another series of slice images showing nearly the same body part as the body part shown in that slice image may be displayed.

Furthermore, in the embodiment, the slice image associating information is stored in the slice image associating information storage part 82, however, the slice image associating information may be added to the slice images as image supplementary information or tag.

Moreover, in the embodiment, two series of slice images (two series of slice images obtained at this inspection and the previous inspection) are displayed, however, three or more series of slice images can be displayed. In this case, one series of slice image (e.g., one series of slice images obtained at this inspection) may be associated with the other two ore more series of slice images.

INDUSTRIAL APPLICABILITY

The present invention can be used in a medical image display processing apparatus for displaying medical images based on image data acquired by a medical imaging modality, and a medical image display processing program used in the apparatus.

The invention claimed is:

1. A medical image display processing apparatus for causing a display unit to display an axial image based on image data representing one series of axial images which are tomographic images showing cross sectional surfaces substantially perpendicular to a body axis of an object to be inspected and obtained by imaging the object along a body axis direction in predetermined order, said apparatus comprising:
a part recognition unit configured to recognize a body part shown in each axial image of the one series of axial images; and
a display processing unit configured to cause said display unit to display an axial image included in the one series of axial images, and cause, when receiving a body part change instruction, said display unit to display an axial image showing a different body part from the body part of the axial image being displayed on said display unit based on a recognition result of said part recognition unit.

2. The medical image display processing apparatus according to claim 1, wherein:
said part recognition unit generates identification information for identifying two axial images located at a boundary between adjacent two parts; and
said display processing unit causes, when receiving the body part change instruction, said display unit to display an axial image located at a boundary of a desired body part by using said identification information.

3. The medical image display processing apparatus according to claim 1, wherein said display processing unit causes, when receiving no body part change instruction, said display unit to display an axial image according to predetermined initial display information from among the one series of axial images.

4. The medical image display processing apparatus according to claim 1, further comprising:
a schema display processing unit configured to cause said display unit to display a schema representing a human body for selecting a body part;
wherein said display processing unit causes said display unit to display an axial image corresponding to the body part selected in said schema.

5. The medical image display processing apparatus according to claim 1, wherein said part recognizing means includes:
a part determination processing unit configured to tentatively determine a body part shown in each of one series of axial images; and
a part correction processing unit configured to correct the body part tentatively determined with respect to at least one axial image by said part determination processing unit based on information on the one series of axial images.

6. The medical image display processing apparatus according to claim 1, wherein said part recognition unit recognizes at least two of a head, a neck, a chest, an abdomen, a pelvis, a leg, a lung field, a boundary area of adjacent two thereof, and a mixture area including plural areas thereof, as body parts.

7. The medical image display processing apparatus according to claim 1, wherein said part recognition unit tentatively determines a body part shown in each axial image of the one series of axial images based on feature quantity of a cross sectional surface shown in the axial image, and then corrects the body part tentatively determined with respect to at least one axial image based on three-dimensional information on the object represented by the one series of axial images arranged in the predetermined order, thereby recognizes a body part shown in each axial image of the one series of axial images.

8. The medical image display processing apparatus according to claim 7, wherein said part recognition unit tentatively determines a body part shown in each axial image of the one series of axial images based on at least one of (i) feature quantity calculated based on a shape of the cross sectional surface shown in the axial image, (ii) feature quantity of air region within the cross sectional surface shown in the axial image, and (iii) feature quantity of bone region within the cross sectional surface shown in the axial image.

9. The medical image display processing apparatus according to claim 7, wherein said part recognition unit corrects the body part tentatively determined with respect to at least one axial image based on at least one of (i) information on body parts tentatively determined with respect to the one series of axial images arranged in the predetermined order, and (ii) information on a change in the feature quantity of the one series of axial images along the body axis direction.

10. A medical image display processing apparatus for causing a display unit to display plural axial images based on image data representing plural series of axial images which are tomographic images showing cross sectional surfaces substantially perpendicular to a body axis of an object to be inspected and obtained by imaging the object along a body axis direction in predetermined order, said apparatus comprising:

a part recognition unit configured to recognize a body part shown in each axial image of the plural series of axial images; and a display processing unit configured to cause said display unit to display an axial image included in one series of axial images, and cause said display unit to display an axial image included in another series of axial images showing a substantially same body part as the body part shown in the axial image being displayed on said display unit based on a recognition result of said part recognition unit.

11. The medical image display processing apparatus according to claim 10, wherein said display processing unit includes:

an axial image associating processing part configured to associate each axial image of one series of axial images with respective one axial image of another series of axial images showing a substantially same body part as the body part shown in each axial image of the one series of axial images based on a recognition result of said part recognition unit; and an axial image display processing part configured to cause said display unit to display an axial image included in the one series of axial images, and cause said display unit to display an axial image included in the other series of axial images and associated with the axial image being displayed on said display unit.

12. The medical image display processing apparatus according to claim 10, wherein said part recognition unit tentatively determines a body part shown in each axial image of the plural series of axial images based on feature quantity of a cross sectional surface shown in the axial image, and then corrects the body part tentatively determined with respect to at least one axial image based on three-dimensional information on the object represented by each series of axial images arranged in the predetermined order, thereby recognizes a body part shown in each axial image of the plural series of axial images.

13. The medical image display processing apparatus according to claim 12, wherein said part recognition unit tentatively determines a body part shown in each axial image of the plural series of axial images based on at least one of (i) feature quantity calculated based on a shape of the cross sectional surface shown in the axial image, (ii) feature quantity of air region within the cross sectional surface shown in the axial image, and (iii) feature quantity of bone region within the cross sectional surface shown in the axial image.

14. The medical image display processing apparatus according to claim 12, wherein said part recognition unit corrects the body part tentatively determined with respect to at least one axial image based on at least one of (i) information on body parts tentatively determined with respect to each series of axial images arranged in the predetermined order, and (ii) information on a change in the feature quantity of each series of axial images along the body axis direction.

15. A non-transitory computer readable medium encoded with a processing program for causing a display unit to display an axial image based on image data representing one series of axial images which are tomographic images showing cross sectional surfaces substantially perpendicular to a body axis of an object to be inspected and obtained by imaging the object along a body axis direction in predetermined order, said medium configuring, when implemented on a computer, the computer to perform steps of:

(a) recognizing a body part shown in each axial image of the one series of axial images;

(b) causing said display unit to display an axial image included in the one series of axial images; and (c) causing, when receiving a body part change instruction, said display unit to display an axial image showing a different body part from the body part of the axial image being displayed on said display unit based on a recognition result at step (a).

16. The non-transitory computer readable medium according to claim 15, wherein:

step (a) includes generating identification information for identifying two axial images located at a boundary between adjacent two parts; and step (c) includes causing, when receiving the body part change instruction, said display unit to display an axial images located at a boundary of a desired body part by using said identification information.

17. The non-transitory computer readable medium according to claim 15, wherein step (b) includes causing said display unit to display an axial image according to predetermined initial display information from among the one series of axial images.

18. The non-transitory computer readable medium according to claim 15, configuring the computer to further perform step of:

(b') causing said display unit to display a schema representing a human body for selecting a body part;

wherein step (c) includes causing said display unit to display an axial image corresponding to the body part selected in said schema.

19. The non-transitory computer readable medium according to claim 15, wherein procedure (a) includes the procedures of:

(a1) tentatively determining a body part shown in each of one series of axial images; and (a2) correcting the body part tentatively determined with respect to at least one axial image at procedure (a1) based on information on the one series of axial images.

20. The non-transitory computer readable medium according to claim 15, wherein step (a) includes recognizing at least two of a head, a neck, a chest, an abdomen, a pelvis, a leg, a lung field, a boundary area of adjacent two thereof, and a mixture area including plural areas thereof, as body parts.

21. The non-transitory computer readable medium according to claim 15 wherein step (a) includes tentatively determining a body part shown in each axial image of the one series of axial images based on feature quantity of a cross sectional surface shown in the axial image, and then correcting the body part tentatively determined with respect to at least one axial image based on three-dimensional information on the object represented by the one series of axial images arranged in the predetermined order, thereby recognizing a body part shown in each axial image of the one series of axial images.

22. The non-transitory computer readable medium according to claim 21, wherein step (a) includes tentatively determining a body part shown in each axial image of the one series of axial images based on at least one of (i) feature quantity calculated based on a shape of the cross sectional surface shown in the axial image, (ii) feature quantity of air region within the cross sectional surface shown in the axial image, and (iii) feature quantity of bone region within the cross sectional surface shown in the axial image.

23. The non-transitory computer readable medium according to claim 21, wherein step (a) includes correcting the body part tentatively determined with respect to at least one axial image based on at least one of (i) information on body parts tentatively determined with respect to the one series of axial images arranged in the predetermined order, and (ii) information on a change in the feature quantity of the one series of axial images along the body axis direction.

24. A non-transitory computer readable medium encoded with a processing program for causing a display unit to display plural axial images based on image data representing plural series of axial images which are tomographic images showing cross sectional surfaces substantially perpendicular to a body axis of an object to be inspected and obtained by imaging the object along a body axis direction in predetermined order, said medium configuring, when implemented on a computer, the computer to perform steps of:
   (a) recognizing a body part shown in each axial image of the plural series of axial images;
   (b) causing said display unit to display an axial image included in one series of axial images; and
   (c) causing said display unit to display an axial image included in another series of axial images showing a substantially same body part as the body part shown in the axial image being displayed on said display unit based on a recognition result at step (a).

25. The non-transitory computer readable medium according to claim 24, wherein step (c) includes the steps of:
   (c1) associating each axial image of one series of axial images with respective one axial image of another series of axial images showing a substantially same body part as the body part shown in each axial image of one series of axial images based on a recognition result at step (a); and
   (c2) causing said display unit to display an axial image included in the other series of axial images and associated with the axial image being displayed at step (b).

26. The non-transitory computer readable medium according to claim 24 wherein step (a) includes tentatively determining a body part shown in each axial image of the plural series of axial images based on feature quantity of a cross sectional surface shown in the axial image, and then correcting the body part tentatively determined with respect to at least one axial image based on three-dimensional information on the object represented by each series of axial images arranged in the predetermined order, thereby recognizing a body part shown in each axial image of the plural series of axial images.

27. The non-transitory computer readable medium according to claim 26, wherein step (a) includes tentatively determining a body part shown in each axial image of the plural series of axial images based on at least one of (i) feature quantity calculated based on a shape of the cross sectional surface shown in the axial image, (ii) feature quantity of air region within the cross sectional surface shown in the axial image, and (iii) feature quantity of bone region within the cross sectional surface shown in the axial image.

28. The non-transitory computer readable medium according to claim 26, wherein step (a) includes correcting the body part tentatively determined with respect to at least one axial image based on at least one of (i) information on body parts tentatively determined with respect to each series of axial images arranged in the predetermined order, and (ii) information on a change in the feature quantity of each series of axial images along the body axis direction.

* * * * *